(12) United States Patent
Courtion et al.

(10) Patent No.: US 11,116,691 B2
(45) Date of Patent: *Sep. 14, 2021

(54) LIGHT-EMITTING DIODE AND MASSAGE DEVICE FOR DELIVERING FOCUSED LIGHT FOR VAGINAL REJUVENATION

(71) Applicant: Joylux, Inc., Seattle, WA (US)

(72) Inventors: Colette Courtion, Seattle, WA (US); Nicolas Loebel, Woodinville, WA (US); Roger Andersen, Ladysmith (CA); Kevin Bailey, Ottawa (CA); Matthew Bailey, Ottawa (CA); Yana Klimava, Gatineau (CA)

(73) Assignee: Joylux, Inc., Seattle, WA (US)

( * ) Notice: Subject to any disclaimer, the term of this patent is extended or adjusted under 35 U.S.C. 154(b) by 344 days.

This patent is subject to a terminal disclaimer.

(21) Appl. No.: 16/201,941

(22) Filed: Nov. 27, 2018

(65) Prior Publication Data
US 2019/0091097 A1   Mar. 28, 2019

Related U.S. Application Data

(63) Continuation of application No. 14/874,322, filed on Oct. 2, 2015, now Pat. No. 10,179,085.

(51) Int. Cl.
*A61H 19/00* (2006.01)
*A61H 21/00* (2006.01)
(Continued)

(52) U.S. Cl.
CPC ............. *A61H 19/40* (2013.01); *A61H 19/44* (2013.01); *A61H 23/0263* (2013.01);
(Continued)

(58) Field of Classification Search
CPC .... A61H 19/40; A61H 19/44; A61H 23/0263; A61H 2201/0153; A61H 2201/0188;
(Continued)

(56) References Cited

U.S. PATENT DOCUMENTS 4,742,235 A * 5/1988 Koji .................. A61B 18/20
                                              250/504 R
6,741,895 B1   5/2004 Gafni et al.
(Continued)

FOREIGN PATENT DOCUMENTS

CN         2907735 Y    6/2007
CN      101080210 A    11/2007
(Continued)

OTHER PUBLICATIONS

United States Office Action, U.S Appl. No. 16/157,047, dated Mar. 22, 2019, 21 pages.
(Continued)

*Primary Examiner* — Timothy A Stanis
(74) *Attorney, Agent, or Firm* — Fenwick & West LLP

(57) ABSTRACT

A rejuvenation and massage device is provided for treating mucosa tissue, such as vaginal tissue, affected by Vaginal Relaxation Syndrome (VRS) or other conditions, through vibration, thermal loading, and light emittance for a duration of time. In one embodiment, the device is an insertable device that includes Low-Level Laser Light (LLLT) therapy to treat the vaginal tissue. The light emittance by one or more light emitters is in a range sufficient to provide therapeutic effects through light radiation. To enhance the therapeutic effects of light radiation provided by the device, the device is configured to provide increased energy density into target tissue of vaginal muscles though a light configuration component (e.g., a focusing component, such as a concave lens assembly, a convex assembly, a pre-lensed light emitter or other focusing optical mechanism) associated with the light emitter that concentrates the light emitted from the light emitter.

23 Claims, 15 Drawing Sheets

(51) Int. Cl.
*A61N 5/06* (2006.01)
*A61H 23/02* (2006.01)
*A61N 5/067* (2006.01)

(52) U.S. Cl.
CPC .... *A61N 5/0603* (2013.01); *A61H 2201/0153* (2013.01); *A61H 2201/0188* (2013.01); *A61H 2201/0207* (2013.01); *A61H 2201/0214* (2013.01); *A61H 2201/0242* (2013.01); *A61H 2201/0278* (2013.01); *A61H 2201/0285* (2013.01); *A61H 2201/10* (2013.01); *A61H 2201/1463* (2013.01); *A61H 2201/169* (2013.01); *A61H 2201/5007* (2013.01); *A61H 2201/5028* (2013.01); *A61H 2201/5038* (2013.01); *A61H 2201/5082* (2013.01); *A61H 2201/5092* (2013.01); *A61N 2005/067* (2013.01); *A61N 2005/0611* (2013.01); *A61N 2005/0626* (2013.01); *A61N 2005/0659* (2013.01); *A61N 2005/0663* (2013.01)

(58) Field of Classification Search
CPC .... A61H 2201/0207; A61H 2201/0214; A61H 2201/0242; A61H 2201/0278; A61H 2201/0285; A61H 2201/10; A61H 2201/1463; A61H 2201/169; A61H 2201/5007; A61H 2201/5028; A61H 2201/5038; A61H 2201/5082; A61H 2201/5092; A61N 5/0603
See application file for complete search history.

(56) References Cited

U.S. PATENT DOCUMENTS

| | | | |
|---|---|---|---|
| 7,351,252 B2 | 4/2008 | Altshuler | |
| 7,452,326 B2 | 11/2008 | Fladl et al. | |
| 7,526,344 B2 | 4/2009 | Kim | |
| 8,679,170 B2 | 3/2014 | Muehlbauer et al. | |
| 8,786,689 B1* | 7/2014 | Liu | A61B 1/0638 348/68 |
| 8,801,600 B2 | 8/2014 | Zipper | |
| 8,961,511 B2 | 2/2015 | Parmer | |
| 9,271,785 B2 | 3/2016 | Parmer et al. | |
| 9,415,235 B2 | 8/2016 | Galen et al. | |
| 9,949,889 B2 | 4/2018 | Courtion et al. | |
| 10,166,168 B2 | 1/2019 | Courtion et al. | |
| 10,179,085 B2 | 1/2019 | Courtion et al. | |
| 2002/0156402 A1 | 10/2002 | Woog et al. | |
| 2002/0198576 A1 | 12/2002 | Chen et al. | |
| 2006/0103905 A1 | 5/2006 | Walmsley | |
| 2006/0271024 A1 | 11/2006 | Gertner et al. | |
| 2007/0015952 A1 | 1/2007 | Chang et al. | |
| 2008/0058783 A1* | 3/2008 | Altshuler | A61B 18/20 606/9 |
| 2008/0065187 A1 | 3/2008 | Squicciarini | |
| 2009/0319008 A1* | 12/2009 | Mayer | A61N 5/0603 607/90 |
| 2010/0022922 A1 | 1/2010 | Barthe et al. | |
| 2010/0049283 A1* | 2/2010 | Johnson | A61N 5/0616 607/89 |
| 2010/0174136 A1 | 7/2010 | Shim | |
| 2010/0241196 A1 | 9/2010 | Meyer | |
| 2011/0190689 A1 | 8/2011 | Bennett et al. | |
| 2011/0224584 A1 | 9/2011 | Pryor et al. | |
| 2012/0136287 A1 | 5/2012 | Barnard et al. | |
| 2012/0179229 A1 | 7/2012 | Tettamanti et al. | |
| 2013/0030507 A1 | 1/2013 | Mayer | |
| 2013/0053630 A1 | 2/2013 | Wail et al. | |
| 2013/0261385 A1* | 10/2013 | Zipper | A61H 19/34 600/38 |
| 2014/0088668 A1 | 3/2014 | Kim et al. | |
| 2014/0350334 A1 | 11/2014 | Zipper | |
| 2015/0133832 A1 | 5/2015 | Courtion et al. | |
| 2015/0273236 A1 | 10/2015 | Rogers | |
| 2015/0327926 A1 | 11/2015 | Parmer | |
| 2016/0000642 A1 | 1/2016 | Zipper | |
| 2016/0129278 A1 | 5/2016 | Mayer | |
| 2016/0135876 A1 | 5/2016 | Parmer et al. | |
| 2017/0028213 A1 | 2/2017 | Courtion et al. | |
| 2017/0071651 A1 | 3/2017 | Allan et al. | |
| 2019/0038501 A1 | 2/2019 | Courtion et al. | |

FOREIGN PATENT DOCUMENTS

| | | |
|---|---|---|
| CN | 101293124 A | 10/2008 |
| CN | 102971047 A | 3/2013 |
| EP | 3068361 A2 | 5/2015 |
| GB | 2366734 A | 3/2002 |
| JP | 2008-532578 A | 8/2008 |
| JP | 2013-505069 A | 2/2013 |
| WO | WO 2005/046792 A1 | 5/2005 |
| WO | WO 2006/103678 A2 | 10/2006 |
| WO | WO 2007/092610 A2 | 8/2007 |
| WO | WO 2007/107105 A1 | 9/2007 |
| WO | WO 2013/016590 A1 | 1/2013 |
| WO | WO 2013/027135 A1 | 2/2013 |
| WO | WO 2015/070242 A2 | 5/2015 |

OTHER PUBLICATIONS

Hattori, S., "Collagen as an Animal Derived Fibrous Protein—its Character and Application," Fiber and Industry, vol. 65, No. 12, pp. 453-461, Japan, 2009. (With English Abstract).

Canadian Intellectual Property Office, Office Action, Canadian Patent Application No. 2,930,252, dated Dec. 5, 2019, 5 pages.

Boreham, M et al., "Anal Incontinence in Women Presenting for Gynecologic Care: Prevalence, Risk Factors, and Impact upon Quality of Life", American Journal of Obstetrics and Gynecology, 2005, vol. 192, pp. 1637-1642.

Chang, R., "Chemical Kinetics," Physical Chemistry for the Chemical and Biological Sciences, Chapter 12, pp. 445-509, 3rd Ed. Sausalito, CA: University Science Books; 2000.

Chiquet, M. et al., "Regulation of Extracellular Matrix Synthesis by Mechanical Stress", Biochemistry and Cell Biology, 1996, vol. 74, pp. 737-744.

Delancey, J et al., "Comparison of Levator Ani Muscle Defects and Function in Women with and without Pelvic Organ Prolapse", Obstetrical and Gynecological Survey, 2007, vol. 109, pp. 295-302.

European Patent Office, Extended Search Report and Opinion, European Patent Application No. 14860017.4, dated Jul. 21, 2017, nine pages.

Fagnani, F. et al., "The Effects of a Whole-Body Vibration Program on Muscle Performance and Flexibility in Female Athletes", American Journal of Physical Medicine & Rehabilitation, 2006, vol. 85, No. 12, pp. 956-962.

Fultz, N et al., "Burden of Stress Urinary Incontinence for Community-Dwelling Women", American Journal of Obstetrics and Gynecology, 2003, vol. 189, pp. 1275-1282.

Hayashi, K. et al., "Effect of Nonablative Laser Energy on the Joint Capsule: An In Vivo Rabbit Study Using a Holmium: YAG Laser", Lasers in Surgery and Medicine, 1997, vol. 20, issue 2, pp. 164-171.

Hayashi, K. et al., "The Effect of Thermal Heating on the Length and Histologic Properties of the Glenohumeral Joint Capsule", The American Journal of Sports Medicine, 1997, 25(1), pp. 107-112.

Kushikata N. et al., "Is Topical Anesthesia Useful in Noninvasive Skin Tightening Using Radiofrequency?", Dermatol Surg, 2005, vol. 31, pp. 526-533.

Lee, C. et al., "Nanofiber Alignment and Direction of Mechanical Strain Affect the ECM Production of Human ACL Fibroblast", Biomaterials, 2005, vol. 26, No. 11, pp. 1261-1270.

Leikina, E., et al., "Type I Collagen is Thermally Unstable at Body Temperature", Proc. Natl. Acad. Sci., 2002, vol. 99, No. 3, pp. 1314-1318.

Lukacz, E et al., "Parity, Mode of Delivery, and Pelvic Floor Disorders", American College of Obstetricians and Gynecologists, 2006, vol. 107, No. 6, pp. 1253-1260.

(56) References Cited

OTHER PUBLICATIONS

Olsen, A. et al, "Epidemiology of Surgically Managed Pelvic Organ Prolapse and Urinary Incontinence", Obstetrics & Gynecology, 1997, vol. 89, No. 4, pp. 501-506.

PCT International Search Report and Written Opinion, PCT Application No. PCT/US2016/54242, dated Dec. 20, 2016, eleven pages.

Pre, D. et al., "High-Frequency Vibration Treatment of Human Bone Marrow Stromal Cells Increases Differentiation toward Bone Tissue", Hindawi Publishing Corporation, Bone Marrow Research, vol. 2013, Article ID 803450, 13 pages.

Rahn, D et al., "Effect of Vaginal Distention on Elastic Fiber Synthesis and Matrix Degradation in the Vaginal Wall: Potential Role in the Pathogenesis of Pelvic Organ Prolapse", American Journal of Physiology—Regulatory, Integrative, and Comparative Physiology, Oct. 2008, vol. 295, No. 4, pp. R1351-R1358.

Rodrigues Dos Santos, R. et al., "The Low-Level Laser Therapy on Muscle Injury Recovery: Literature Review", J Health Sci Inst., 2010, 28(3):286-288.

Ruoslahti, E., "Stretching is Good for a Cell", Science, 1997, vol. 276, No. 5317, pp. 1345-1346.

Second Office Action for Chinese Patent Application No. CN 201480072622.3, dated Nov. 30, 2017, 32 pages.

State Intellectual Property Office of the People's Republic of China, First Office Action, Chinese Patent Application No. 201480072622.3, dated Mar. 20, 2017, twenty-six pages.

Takeuchi, R. et al., "Effects of Vibration and Hyaluronic Acid on Activation of Three-Dimensional Cultured Chondrocytes", Arthritis & Rheumatism, 2006, 54(6), pp. 1897-1905.

Tirkkonen L. et al., "The Effects of Vibration Loading on Adipose Stem Cell Number, Viability and Differentiation Towards Bone-Forming Cells", Journal of Royal Society Interface, 2011, 8(65), pp. 1736-1747.

Varma, M et al., "Fecal Incontinence in Females Older than Aged 40 Years: Who is at Risk?", Dis Colon Rectum, 2006, vol. 49, pp. 841-851.

Wang, C. et al., "Low-Magnitude Vertical Vibration Enhances Myotube Formation in C2C12 Myoblasts", Journal of Applied Physiology, 2010, vol. 109 No. 3, pp. 840-848.

China National Intellectual Property Administration, Office Action, CN Patent Application No. 201910638348.6, dated Feb. 2, 2021, 21 pages.

* cited by examiner

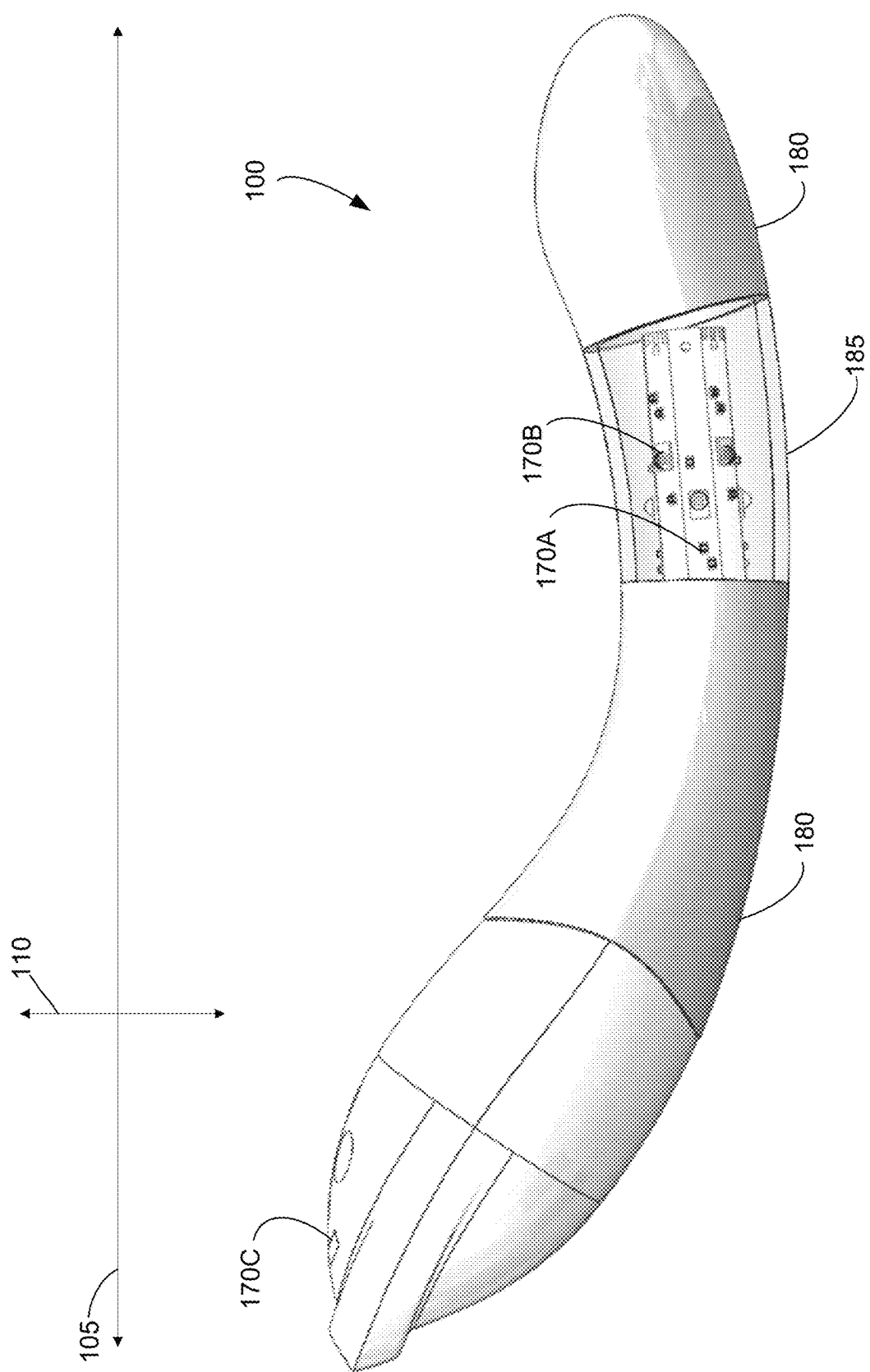

LIGHT-EMITTING DIODE AND MASSAGE DEVICE FOR DELIVERING FOCUSED LIGHT FOR VAGINAL REJUVENATION

CROSS REFERENCE TO RELATED APPLICATIONS

This application is a continuation of prior, co-pending U.S. application Ser. No. 14/874,322, filed on Oct. 2, 2015, the content of which is incorporated herein by reference in its entirety for all purposes.

BACKGROUND

This invention relates generally to vaginally-insertable devices, more specifically to vaginal rejuvenation insertable devices, which provide increased energy density into target tissue of vaginal muscles, and enhance the therapeutic effects of light radiation provided by the devices.

After child birth or with aging, women can experience weakening or relaxing of their vaginal muscles. This relaxation of vaginal muscle is known as Vaginal Relaxation Syndrome (VRS) or vaginal wall distension and it negatively impacts sexual intercourse, can cause intimacy and self-esteem problems, and can lead to urinary incontinence. Conventional solutions for tightening relaxed vaginal muscle include kegel exercises and vaginal creams, but these are generally ineffective. Costly and invasive procedures for vaginal rejuvenation (e.g., vaginoplasty or laser vaginal rejuvenation) are another option, but these also fail to provide a safe, comfortable, affordable option for vaginal rejuvenation. Clinical treatment devices for insertion into the vagina to provide treatment are also available. However, the ability of these conventional devices to actually treat VRS appears to be limited. Furthermore, these devices are for treatment in a clinical setting, and are not designed a compact device for consumer or home use, nor are they designed to be enjoyable for the woman to use, making it less likely that regular treatments will occur and decreasing effectiveness of the devices.

SUMMARY

A rejuvenation and massage device for the vaginal lumen includes an insertable device that repairs mucosa tissue, such as vaginal tissue, after VRS for example, through vibration, thermal loading, and light emittance for a duration of time. In one embodiment, the device includes Low-Level Laser Light (LLLT) therapy to treat the vaginal tissue. The light emittance by one or more light emitters is in a range sufficient to prevent apoptosis and cell death, stimulate fibroblast proliferation, migration and collagen synthesis, modulate inflammatory and anti-oxidant responses, and/or simulate angiogenesis and tissue repair in the vaginal tissue.

To enhance the therapeutic effects of light radiation provided by the device, the device is configured to provide increased energy density into target tissue of vaginal muscles though a light configuration component. The light configuration component is associated with one or more light emitters of the device and is configured to increase the energy density deposited into the target tissue of vaginal muscles of a user of the device. For example, the light configuration component is configured to concentrate the light emitted from a light emitter via a focusing component, e.g., a concave lens assembly, a convex assembly, a pre-lensed light emitter or other focusing optical mechanism, on above or top of the light emitter. The focusing component is configured to refract the light emitted from the light emitter, which increases the power density being delivered to the vaginal tissue contacted by the device without using disproportionately more battery power, without increasing the heat output from the light emitters, and without risking damage to the device or to the users of the device.

To repair mucosa tissue, such as vaginal tissue, through vibration, the device applies a controlled amount of heat to the subdermal connective tissues surrounding the vaginal mucosa, in particular to the vaginal mucosa of post-parous women who have experienced significant loss of vaginal tone and tissue tension due to tissue stretching, elastase enzyme production, hypoxia, and mechanical stress during birth. The mechanism of action is primarily collagenous remodeling within connective tissue surrounding the vaginal canal in a sequential process starting with collagen melting and ending with inflammatory and fibrotic responses generating significant tightening of the vaginal lumen. In some embodiments, the heat is applied at a temperature range sufficient to induce neocollagenesis, neofibrogenesis, or neoelastogenesis.

The device also vibrates to provide massage to the tissue, and this vibration may also increase the healing response in the vaginal tissue. The massage induces a pleasure response in the user, making the device enjoyable to use and encouraging longer use of the device. Since the device is used for a greater length of time, a controlled application of heat at a lower level can occur for a greater length of time to more effectively induce collagen melting. With the application of vibration, it is possible to enhance the processes of neoelastogenesis and neocollagenesis, thereby providing more effective repair and tightening to the vaginal tissue. Thus, the vibration may be applied at a range that provides a pleasure response in the user. The vibration may also be applied at a range sufficient to enhance myofibril generation and neocollagenesis while inducing a pleasure response.

The device can be designed to be a convenient at-home use device that can be manipulated by untrained users. In one embodiment, the device is a handheld device and most or all of the components are integrated within the handheld device. The device can have a variety of settings that can be controlled by the user or automatically by the device. The device can also be designed to treat localized areas of intravaginal tissue rather than the entire length of the vaginal lumen, thereby increasing the rate of healing from adjacent untreated tissue sites. The device can also be used with certain customized lubricants.

BRIEF DESCRIPTION OF THE DRAWINGS

FIGS. 1C-1E are examples of a rejuvenation and massage device, in accordance with an embodiment.

Figure 1A:
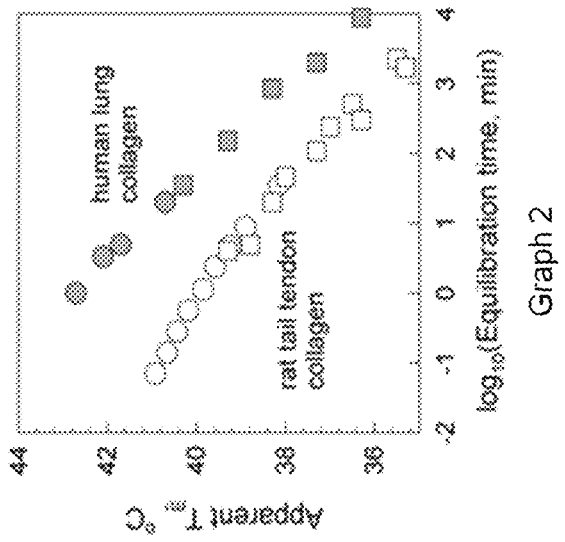
FIGS. 1A-1B are graphs illustrating data associated with skin repair, in accordance with an embodiment.
Figure 1A:
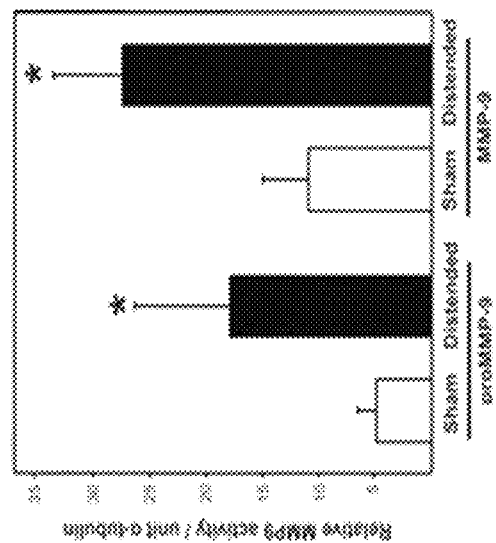
Figure 1A:
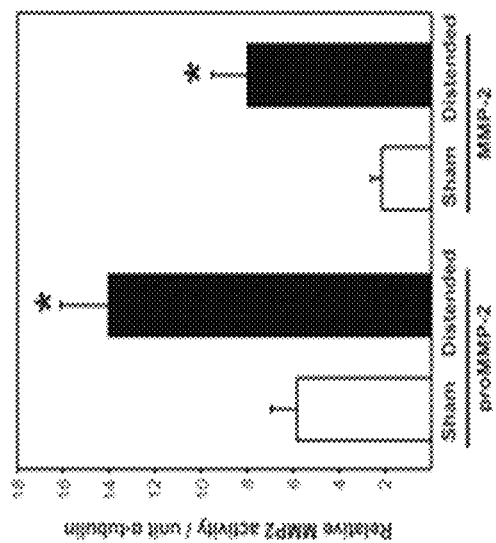
Figure 1A:
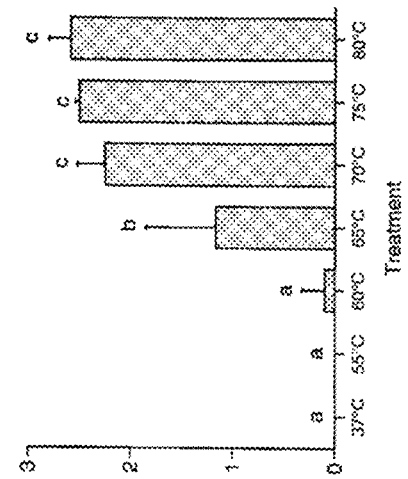
Figure 1A:
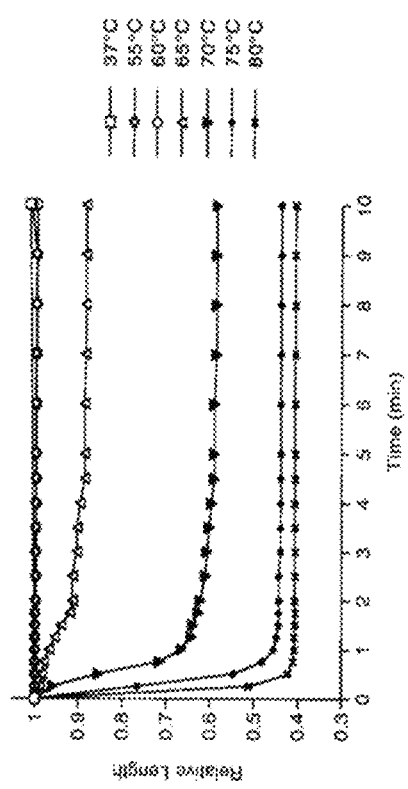

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION (a) Overview

Effects of Childbirth on Vaginal Walls

After child birth or with aging, women can experience the weakening or relaxing of their vaginal muscles. For example, childbirth can cause plastic vaginal wall distension, also known as Vaginal Relaxation Syndrome (VRS). Peer-reviewed literature reveals that childbirth is associated with a four- to seven-fold increase (1) in several pelvic floor disorders including plastic vaginal distension, urinary and fecal incontinence, and pelvic organ prolapse. Literature suggests that childbirth causes direct muscular trauma or denervation injury of the striated muscles of the pelvic floor (termed the levator ani) and thereby leads to failure of muscular support of pelvic organs. These disorders affect one-third of adult women in the United States, impacting their quality of life (2, 3, 4, 5). One study of 149,554 adult women reported an 11 percent risk of undergoing a single operation for pelvic floor disorders or incontinence by age 80 and found that 29 percent of these women required multiple surgeries (6).

Vaginal wall distension has been shown to result in increased expression of the matrix metalloproteases MMP-2 and MMP-9, elastase enzymes expressed predominantly in connective tissue and bone marrow cells (7). The elastase enzymes are responsible for destruction of elastin, another important protein such as collagen in connective tissue for establishing the spring-like characteristics of connective tissue. Elastin damage reduces the ability of stretched connective tissue to reconform to the original shape after stretching. In experiments carried out in mice, a microballoon is used to stretch the vaginal walls and numerous fragmented and disrupted elastin fibers were seen upon histological examination (7). The upregulation of MMP-2 and -9 production after distension was pronounced as seen in Graph 1(a) and Graph 1(b), respectively, as shown in FIG. 1A.

In addition to the elastase effects, prolonged tissue stretching, hypoxia, and mechanical stress on the vaginal mucosal walls due to childbirth contribute to plastic distension of the organ. Taken together, the results indicate that vaginal wall distension induces increased protease activity and that elastic fiber synthesis is crucial for recovery of the vaginal wall from distension-induced injury.

Reconformation of Collagen and Elastin Fibers

Vaginal muscle tissue structures, the vaginal mucosal walls, and the vaginal muscle tissue, like other tissue in the human body, include an extracellular matrix (ECM) of protein fibers and fibroblast cells within the ECM. To tighten the vaginal muscle tissue, the ECM of protein fibers or, more specifically, the protein fibers themselves can be tightened. The ECM includes fibers of multiple proteins, including collagen, a primary structural protein such as elastin. The collagen protein has a triple helix structure with individual chains held together by hydrogen bonds and provides an elastic, resilient property to tissue due to the individual chains aggregated together, which form fibrils with spring-like tensile properties.

One method of tightening the ECM includes tightening the collagen fibers by denaturing the fibers. Collagen fibers, as well as fibers of other proteins denature and consequently tighten depending on the maximum temperature to which they are exposed. At body temperature, the collagen fibrils form random coils (8). If exposed at temperatures only slightly elevated over normal body temperature, the random coil configuration of collagen changes into a more linear configuration through a process called "melting." This process is time dependent, and is governed by the Arrhenius equation:

$$k = Ae^{-E_a/RT},$$

where k is the rate constant, A the frequency of collisions between reacting molecules, Ea the activation energy, R the gas constant and T the absolute temperature (10). Collagen denaturation, according to the Arrhenius equation, depends on temperature as well as time, as shown in collagen melting temperature data from live tissues in Graph 2 shown in FIG. 1A.

As seen, collagen can melt (denature) at a relatively low temperature when exposed for 5 minutes or longer to a thermal load. Melting can occur at or even below core body temperature. The low melting temperature allows collagen molecules to melt and refold locally, providing elasticity and strength in the connective tissue fibers. The low temperature threshold also permits collagen renaturation (refolding) to occur. At higher temperatures, the collagen protein transitions through a significant configuration change where the fibers contract or tighten, in some cases dramatically, and the reconfiguration or denaturation (e.g., shown in a mean change in tissue length of seven treatment groups during testing) is irreversible as seen in Graph 3 shown in FIG. 1A.

A collagen fiber can contract to about 40% of the original length of the fiber, and then no further changes are possible despite increases in temperature. Collagen contraction initiates at approximately 60° C. and reaches denaturation by 80° C. as seen in subjective histologic scores for collagen structure of the seven treatment groups (mean+/−SD) in Graph 4 shown in FIG. 1A. The bars in Graph 4 with differing letters are significantly different from each other (P<0.05).

The human's perception of thermally-induced pain begins at 40° C. (104° F.), well below the required temperature for significant collagen shortening. Topical cooling can be an approach to this problem because topical anesthetic agents do not appear to increase the patient's tolerance of heat (11).

Once thermally-induced denaturation of the collagen protein and tightening of the ECM has occurred, neoelastogenesis and neocollagenesis occur within a month after the denaturation (12). Neoelastogenesis and neocollagenesis are processes that include remodeling of the ECM as well as integrating new protein fibers, elastin and collagen respectively, in the existing ECM. According to research, these processes initiate seven days after denaturation, a typical timeframe for proliferation of fibroblast cells. The fibroblast cells secrete collagen, assist in the construction of new matrices with the secreted collagen, and effect tissue repair (9). Thermally-induced denaturation will cause contraction of protein fibers and improve tissue tone and connective tissue tension.

Effects of Vibration on Tissue

Research also shows that vibration has an effect on various human cell types (13, 14, 15, 16, 17) including fibroblasts, participants in the remodeling of the ECM. In vivo, there are two ECM glycoproteins, tenascin and collagen XII, specifically expressed in places where mechanical strain is high. Tenascin appears around healing wounds, and is part of the control response involving fibronectin, an important protein involved in collagen binding. Fibroblast cells attached to a strained collagen matrix produce more of the two ECM glycoproteins than fibroblast cells attached to a relaxed collagen matrix (13). Thus, whole body vibration training is widely used in rehabilitation and sports activities to improve muscle strength, balance, and flexibility by utilizing the effect of vibration (18).

Various other studies show that vibration affects the production of proteoglycans, primary proteins found in connective tissue, in 3-dimensional cultured chondrocyte cells in cartilage (19) and enhances formation of a muscle fibril progenitor myotube in female athletes preconditioned with low-magnitude vibration with maximum expression of type I collagen occurring when frequencies of 8-10 Hz were used (16). Low-magnitude vibration has been shown to enhance myotube or muscle fibril formation, with maximum expression of type I collagen occurring when frequencies of 8-10 Hz were used (20).

Figure 1B:
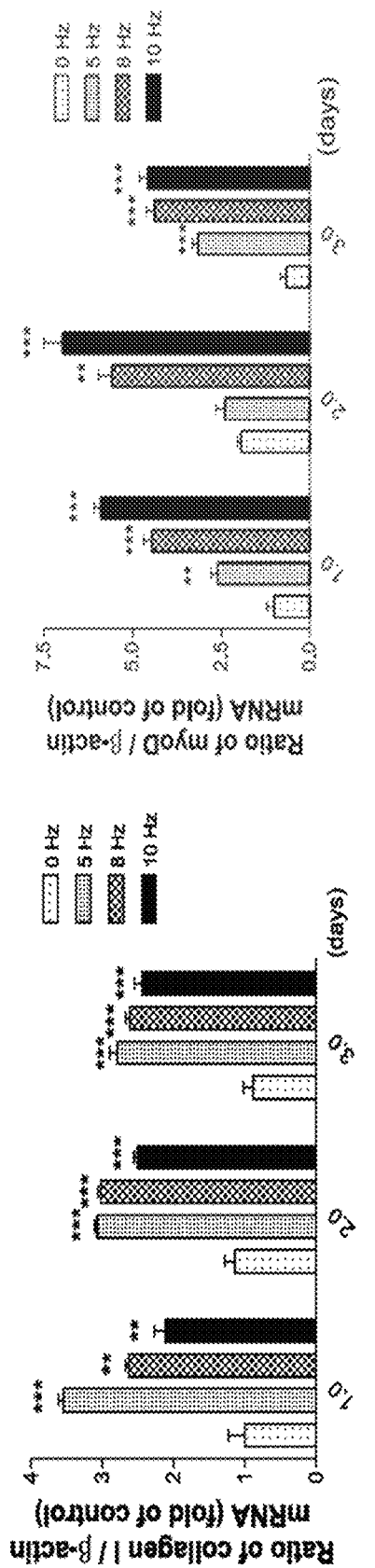
Figure 1B:
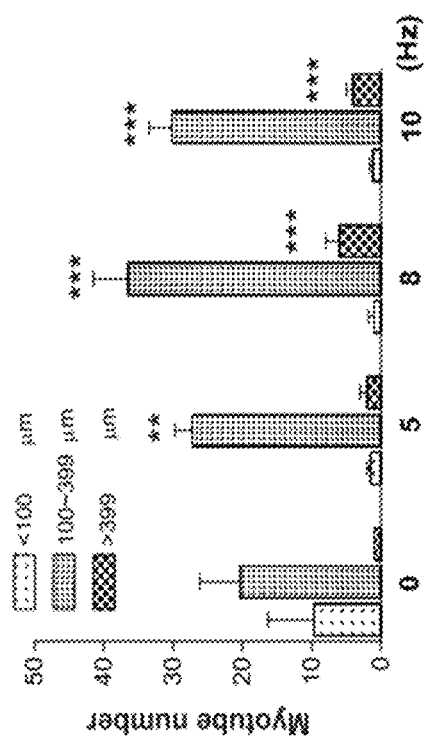

The effects of vibration on the gene expression of type I collagen have been shown to be profound (20) as seen in the effects of vibration on collagen gene upregulation in Graph 5 shown in FIG. 1B. A factor of 3-4× enhancement in gene expression of type I collagen protein and β-actin protein was found. As seen, the largest effects were found at 5 Hz. A factor of greater than 7× was found for gene expression of myoD, a master regulator protein in the early and terminal differential stages of myogenesis, at 10 Hz (20) as seen the effects of vibration on myoD gene upregulation in Graph 6 as shown in FIG. 1B. These gene expression enhancements were mirrored at the cellular level, with myotube number, length, area and fusion index or rate of new cell production all increasing by similar orders of magnitude under the effects of vibration (20) as seen in the effects of vibration on myotube number in Graph 7, as shown in FIG. 1B.

In addition to the effects that vibration has on fibroblasts, the vibration provides the benefit of massaging the vaginal tissue and providing a pleasure response in the user. This additional benefit means that the device may be used more frequently and for a longer period or duration of time, making it easier to have regular, more effective tissue treatments. Collagen is known to melt at around 60° C. to 80° C., though temperatures at 40° C. and above can become uncomfortable to the user. Since a vibrating device is designed to induce pleasure during use, it may be used for a longer period of time. If the time during which heat is applied is extended, it is possible to cause collagen melting at lower temperatures, thus ensuring that the temperatures can remain comfortably within the zone that does not provide pain or discomfort to the user. So, the vibration not only has positive effects on the healing of tissue, but also provides the benefit of making the device enjoyable to use and potentially extending duration of use, allowing for usage of lower temperatures to effect collagen melting, renaturation and subsequent de novo formation.

Effects of Low-Level Laser Light on Tissue

In addition to vibration, research shows that low-level laser light (LLLT) also affects fibroblasts by stimulating fibroblast proliferation, migration and collagen synthesis. Laser light in the deep red portion of the spectrum including some near-infrared portions also prevents apoptosis and cell death, modulates inflammatory and anti-oxidant responses, and stimulates angiogenesis and tissue repair. The LLLT effect is specific to small amounts of light and is now a well-accepted modality for repair of musculoskeletal injuries in athletes (21).

It is also noted that when the light is turned on, the emission pattern of the light diverges rapidly from the light emitters, which may reduce power density (e.g., milliwatts per square centimeter) delivered to the tissue of vaginal muscles. On the other hand, if an uncontrolled amount of additional electrical power is added to the light emitters, the light emitters may heat up quickly and consume disproportionate amounts of battery power of the rejuvenation and massage device.

The disclosed device remodels collagen within connective tissue surrounding the vaginal lumen using one or more of thermal loading, vibration, light emittance, and duration. Thermal loading remodels the ECM by causing collagen to contract, and vibration and light emittance promote activity of the fibroblasts assisting in collagen matrices remodeling. Duration of use can be adjusted depending on the thermal load, or vice versa, to speed up or slow down the thermally-induced denaturation.

The disclosed device is also configured to concentrate the light as it exits the power unit of the device and increase the power density being delivered to the tissue of vaginal muscles, which enhances the therapeutic effects of light radiation provided by the device. For example, the disclosed device can include a lens assembly for each light emitter to generate concentrated light from the light emitter through the lens assembly without using disproportionately more battery power, without increasing heat output from the light emitters, and without risking damage to the light emitters, the device itself or the user of the device.

(b) Rejuvenation and Therapeutic Massage Device

Figure 1C:
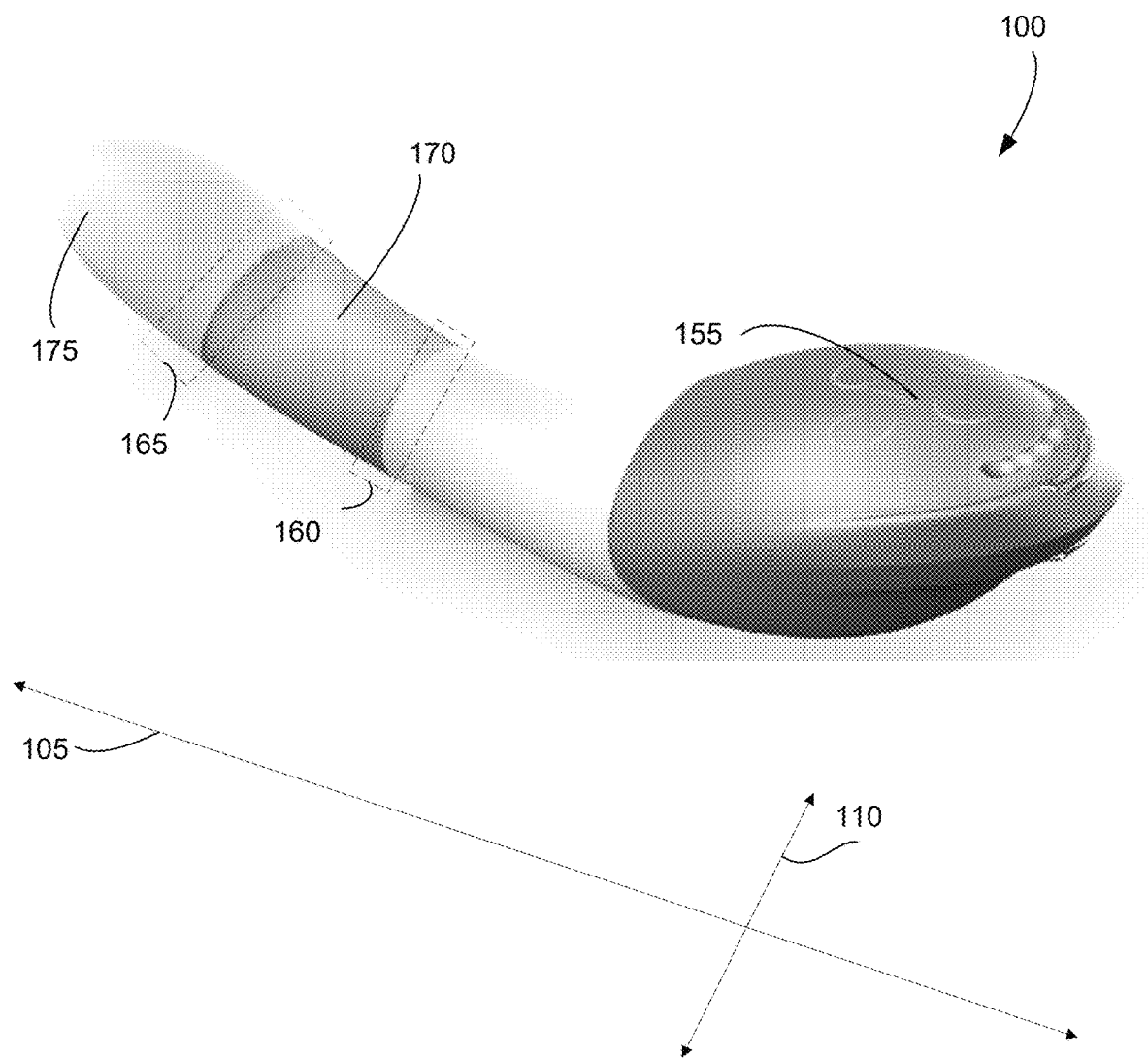
Figure 1D:
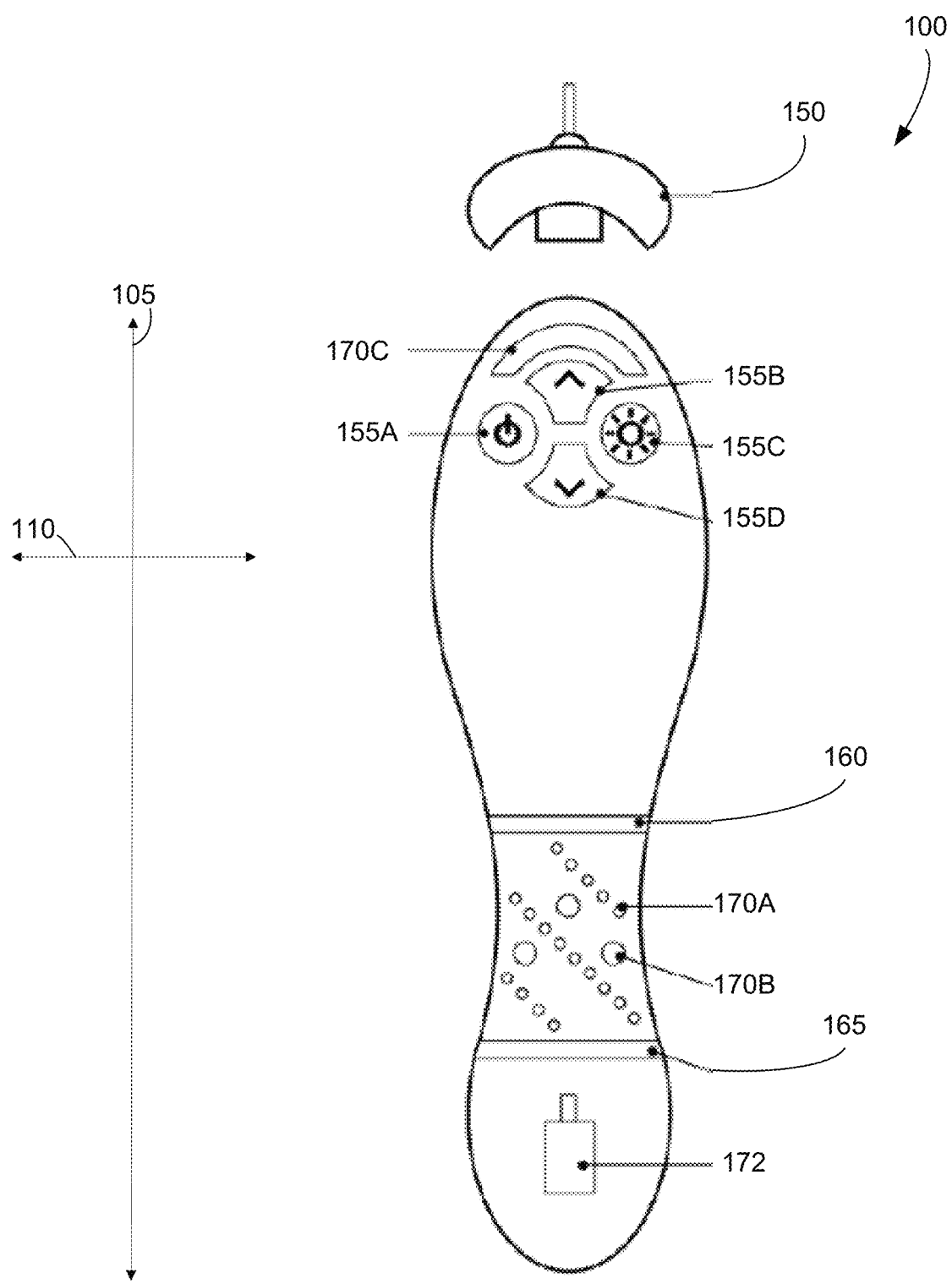

FIGS. 1C-1E are examples of an embodiment of a rejuvenation and therapeutic massage device 100. FIG. 1C provides a perspective view of the device 100, including a handle or end 155 of the device 100, an opposite, insertable end 175 of the device, an area or treatment window 170 between ends 155 and 175, and areas 160 and 165 on either side of the window 170. FIG. 1D is a bottom side diagrammatic view of the device 100 illustrating a user interface, light emitters, and certain internal components. FIG. 1D illustrates controls or buttons 155A-D, charger 150, light emitting diodes 170A-C, portions 160 and 165 that include sensors, and vibrating device 172 (located at end 175 shown in FIG. 1C). FIG. 1E is a side view of the device 100, including illustration of the light emitting diodes 170A-C and showing opaque portions 180 and transparent portion 185 of the device 100.

In the embodiment shown in FIG. 1C, the device is from 2-7 inches long along a vertical axis 105 with a diameter of from 1-3 inches along a horizontal axis 110. In other embodiments, the shape and size of the device 100 may vary. During use, a portion of the device, including at least end 175 and window 170, is placed in the vaginal lumen.

Figure 2:
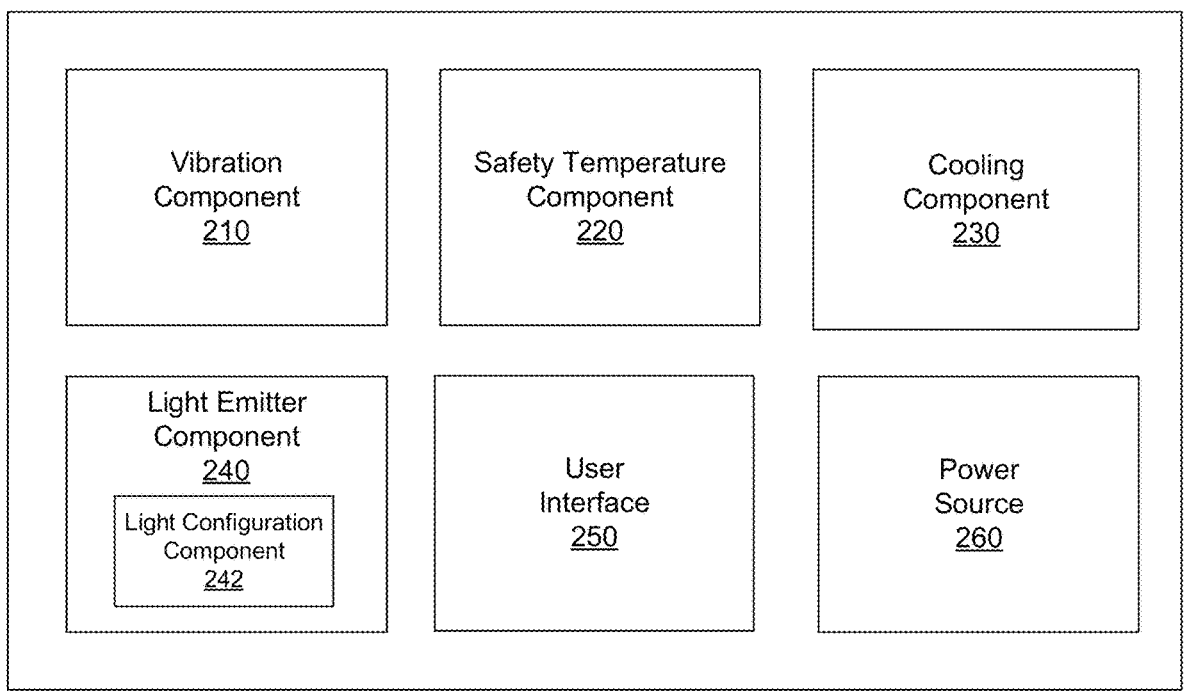
FIG. 2 is a block diagram of components in a rejuvenation and massage device, including a light configuration component for enhancing the therapeutic effects of light radiation provided by the device, in accordance with an embodiment.

FIG. 2 illustrates components that might be found in the device 100 shown in FIGS. 1C-1E, though more or fewer components can be included. According to one embodiment, the device 100 includes a vibration component 210, a safety temperature component 220, a light emitter component 240 having a light configuration component 242, a user interface 250, and a power source 260. In an alternative embodiment, the device includes a vibration component 210, a safety temperature component 220, a cooling component 230, a light emitter component 240, a user interface 250, and a power source 260. For example, in one embodiment as shown in FIG. 1D, the vibration component 210 includes one or more vibration devices 172 (FIG. 1D), such as motors, integrated within the device 100 at end 175, the safety temperature component 220 includes a temperature sensor and/or an optical sensor integrated within a shell of the device and within the device at portions 160 and 165, the light emitter component 240 includes light-emitting diodes at portion 170 (which forms the treatment window for treating the tissue), and the user interface 250 is located at a handle end of the device 100, such as end 155. The light emitter component 240, in this example, includes one or more light emitting diodes 170B for treatment and one or more light emitting diodes 170A and 170C as visual indicators, as shown in FIG. 1D. The handle end of the device such as at end 155 includes one or more controls (e.g., buttons) for turning the device on or off (e.g., 155A in FIG. 1D), turning light therapy on or off (e.g., 155C in FIG. 1D), and for adjusting vibration (e.g., 155B and 155D in FIG. 1D). The light emitter component 240 and user interface are further described below in conjunction with FIG. 2, and the light configuration component 242 of the light emitter component 240 is further described below with reference to FIGS. 7-9.

In one embodiment, the shell of the device is made of a high-durometer medical-grade silicone material, is water-clear in color, and has a very slight deformability in structure. In another embodiment, the shell is made of an opaque liquid crystal polymer. In yet another embodiment, the shell of the device is made of both a high-durometer medical-grade silicone material and a transparent liquid crystal polymer. For example, as shown in a side view in FIG. 1E, the shell of the device 100 can be transparent at a location where light-emitting diodes are located in the device (e.g., at portion 185) and opaque at locations where light-emitting diodes are not located, such as portion 180, as illustrated in FIG. 1E. Portion 185 of the device thus acts as a treatment window and is the area at which light is shone from the device 100 onto tissue inside the vagina to provide treatment to the tissue while the end 175 is inserted in the vagina.

The device can be water-proof (or water-resistant) and can be resistant to a range of lubricant chemistries. The device is thus compatible with use of a customized medical-grade lubricant that matches the refractive index of the optical emitting surface to the tissue surfaces, such as through a water base, maximizing light transmission into the tissue and minimizing loss of light due to scattering.

The device in FIGS. 1C-1E is designed to be an at home use or as a Class 1 product and does not require trained individuals for use. It is also designed to be ergonomic for comfortable and convenient use. It is further portable, easily cleanable, can be battery-operated, and can be IPXn fluid ingress rated. It may be a handheld device, and some or all of the components can be integrated into or included on the device such that it can be a fully-contained consumer handheld unit.

FIGS. 1C-1E provide various examples of how the device could be designed. Other designs of the device can include components for stimulation of certain aspects of the female anatomy. For example, the device might be shaped for or include protrusions that are intended to stimulate the G-spot. The device might also include components that extend from the device outside of the vagina intended for stimulation of the clitoris.

The device can have a variety of massaging features. In some embodiments, it has various vibration settings, including different speeds, tempos or other variations. The vibration settings can also be designed to maximize treatment effectiveness, including generation of the improved healing response caused by vibration. Certain aspects of the device can be designed to rotate or otherwise move to provide massage. The device can include a handle or portion that is gripped by the hand of the user for easy insertion and manipulation, such as handle portion 155 in FIG. 1C, and some or all of the remaining portions of the device can be insertable into the vagina.

FIG. 2 is a block diagram of the components in the rejuvenation and therapeutic massage device in accordance with the embodiment shown in FIG. 1C. In other embodiments, the device may include different and/or additional components than those shown in FIG. 2 and the component may include different and/or additional features than those described herein.

The vibration component 210 applies vibration to the vaginal tissue in contact with the device. The vibration component 210 includes one or more motors and one or more counterweights configured to operate in a 5-10 Hz range, in an 8-10 Hz range, or at any frequency from 0-15 kHz (though it can also operate in other similar ranges, as desired). For example, one motor can operate in a frequency less than 10 Hz to provide vaginal rejuvenation and one or more other motors can operate in a frequency of up to 15 kHz to induce pleasure. As another example, a single motor provides both vaginal rejuvenation and induces pleasure. According to research, the 5-10 Hz range of vibration effects myofibril generation and collagen production, enhancing tissue regeneration, neocollagenesis, and rejuvenation of vaginal tissue. In some embodiments, the vibration component 210 vibrates in whatever range is determined to produce effective myofibril generation and collagen production. The one or more motors and one or more counterweights may be flexibly coupled to the one or more portions of the inner wall of the shell of the device. In one embodiment, the one or more motors and one or more counterweights are coupled to the one or more portions of the inner wall of the shell to maximize surface deflection or maximize offset of the shell to the one or more motors and one or more counterweights. In one embodiment, the one or more motors and one or more counterweights may be coupled inline and paired, providing phases of vibration patterns along the vertical axis 105 of the device. The phases of vibration patterns can be options presented to the user through an external user interface 250. Various vibration patterns can be selected through the user interface 250, as further described below in conjunction with FIG. 3. The vibration component 210 may be coupled to the device to produce vibration along the vertical axis 105 of the device or along the horizontal axis 110 of the device (off-axis movement from the vertical axis 105).

In other embodiments, the vibration component 210 includes a high-efficiency resonant drive mechanism, reducing power required to operate the device. The high-efficiency resonant drive mechanism includes a rare-earth magnetic stator surrounded by laminated armature pieces directing magnetic lines of flux to a spring-steel rotor. The armature includes anti-sense coils and the anti-sense coils periodically and continuously imbalance the magnetic force directed by the armature towards the rotor, causing the rotor to deflect in the direction of applied force. The resonant drive mechanism is configured for resonant operation at any desired frequency, with a preferred range of 5-10 Hz. The resonant drive mechanism can also be configured for resonant operation in an 8-10 Hz range, or at any frequency from 0-15 kHz. For example, one resonant drive mechanism can operate in a frequency less than 10 Hz to provide vaginal rejuvenation and one or more other resonant drive mechanism can operate in a frequency of up to 15 kHz to induce pleasure. A primary attribute of the high-efficiency resonant drive mechanism is that the high-efficiency resonant drive mechanism uses little drive energy for comparatively large mechanical deflections, has no moving or sliding parts which can wear, and includes simple construction not requiring expensive components. In one embodiment, the high-efficiency resonant drive mechanism's rotor is flexibly coupled to the outer walls of the device configured to maximize surface deflection or vibration of key, circumscribed portions of the device, rather than the entire device by default. The flexible coupling maximizes energy coupling to the vaginal mucosa rather than to the hand of a user of the device. In another embodiment, the vibration component 210 includes additional external motors and one or more counterweights attached to an external additional appendage of the device (not shown).

The safety temperature component 220 includes a thermal overload detection including one or more thermocouples, thermal detectors, cutoffs, optical detectors, or other suitable temperature readers or detectors. Therefore, if the temperature of the human mucosa tissue exceeds a threshold temperature as detected by the safety temperature component 220, then the inducement generator 350, described further below in conjunction with FIG. 3, adjusts instructions sent to the light emitter component 240 to lower or turn off LEDs and, therefore, lower temperature through control of emission of the LEDs.

The safety temperature component 220 may also include a safety interlock including a heat sensor in the shell of the device that can detect human tissue (e.g., mucosa tissue) through temperature. In other embodiments, the safety interlock includes infrared sensors or other suitable sensors able to detect human tissue in contact with the outer wall of the shell of the device. The safety interlock can prevent the device, such as through the light emitter component 240, from emitting light or reduce intensity of emitted light if the device is not in contact with the vaginal tissue within the vaginal lumen or equivalent.

The safety temperature component 220 can also heat the vaginal tissue in contact with the device to induce neocollagenesis. The safety temperature component 220 is configured to operate in the range of 35° C.-80° C. to, for example, measure temperature of the shell of the device and/or vaginal mucosa in contact with the shell of the device up to a depth of 7 mm of the vaginal mucosa in contact with the shell of the device, and to allow production of heat preferably to a depth of 5 mm or more on vaginal tissue in contact with the outer wall of the shell of the device, such as the vaginal mucosa. Thus, in this embodiment, the function of the safety temperature component 220 is performed to assist the light emitter component 240. For example, the light emitter component 240 can provide a steady emission of light and thus thermal load while the safety temperature component 220 heats to keep temperature in a temperature range that can be specified by the user or by a protocol stored in memory 360 on the device.

In the embodiment of providing thermal load, the safety temperature component 220 is configured to operate for 1 to 10 minutes, though longer or shorter time periods can be used, as well. For example, in some embodiments, the safety temperature component 220 operates for as long as a user is comfortable and shuts off or cycles at a set temperature when a threshold temperature is reached. Alternatively, the safety temperature component 220 operates for a duration of time dictated by treatment and prior usage. For example, if treatment includes a protocol for use of the device three times a week, each time using the device for 8-10 minutes, the safety temperature component 220 can operate for 8-10 minutes. If, for example, the user has already used the device three times in a week, then duration of the safety temperature component 220 can decrease or an indication can be given to the user that use of the safety temperature component 220 is unnecessary. In some embodiments, the safety temperature component operates in a temperature or range of temperature that is determined to produce heat to a depth that permits collagen melting and repair. The safety temperature component 220 is configured to be able to treat localized areas of vaginal tissue as well as the entire length of the vaginal tissue along the vaginal lumen. Treating localized areas of vaginal tissue allows for a rate of healing higher than when treating the entire length of the vaginal tissue due to assistance from adjacent untreated tissue sites along the vaginal lumen.

The localized areas of vaginal tissue being treated can be selected manually or automatically. In the manual embodiment, the user can use a sliding button with a plurality of notches corresponding to localized areas along the vertical axis 105 of the device. In the automatic embodiment, the safety temperature component 220 selects localized areas along the vertical axis 105 of the device based on one or more programmed patterns stored in memory 360.

To complement the functions of the safety temperature component 220, in some embodiments, the device includes a cooling component 230 that cools the vaginal tissue in contact with the device, minimizing the user's perception of thermal load from the device on the vaginal tissue. Thus, the cooling component 230 can help maintain a temperature of the device in a range or below a threshold temperature. The cooling component 230 includes a coaxial external sheath containing cryogenic fluid, minimizing epithelial heat load. In another embodiment, the cooling component 230 includes one or more Peltier cooling devices integrated into the inner wall of the shell of the device. In other embodiments, the cooling component 230 includes a cooling apparatus peripheral to the inner wall of the shell of the device, minimizing heat load by passive conduction to the inner wall of the shell of the device and then to a heat-pipe assembly. Another embodiment includes a liquid coolant, such as nontoxic propylene glycol in water, which directs excess thermal energy from the light emitter component 240 to a heat exchanger located at one end of the device. The cooling component 230 is configured to cool the vaginal tissue in contact with the device to below 40° C., though it can also be designed to cool to higher or lower temperatures, as desired. The cooling component 230 is an optional component and may or may not be required depending on the safety temperature component 220.

The light emitter component 240 emits light in a spectrum range sufficient to prevent apoptosis and cell death, stimulate fibroblast proliferation, migration and collagen synthesis, modulate inflammatory and anti-oxidant responses, and simulate angiogenesis and tissue repair in the vaginal tissue. The light emitter component 240 can also emit light in a visible spectrum as a visual indicator to provide a user a visual indication in a treatment window 185 that light is being emitted in a spectrum range sufficient to prevent apoptosis and cell death, stimulate fibroblast proliferation, migration and collagen synthesis, modulate inflammatory and anti-oxidant responses, and simulate angiogenesis and tissue repair in the vaginal tissue. A visual indicator can also be included in a handle 155 portion of the device 100 to provide the user an additional visual indicator that is visible during use of the device 100. The light emitter component 240 is configured to apply thermal load of 150 mW/cm$^2$ to a penetration depth of 3-5 mm or up to 7 mm on vaginal mucosa surrounding the device and is controlled based on temperature readings taken by the safety temperature component 220.

In another embodiment, the light emitter component 240 can also emit light in a range of 250-400 nm for disinfection or sterilization purposes. Light emitted in the range of 250-400 nm can kill bacteria and prevent infection, such as yeast infection, during use of the device. The light emitted in the range of 250-400 nm can sterilize and kill bacteria in the vaginal tissue along the treatment portion of the device such as portion 185 in FIG. 1E, along the device itself inserted in the vagina, or both. Thus, this light emitted can act to kill bacteria on the tissue and or on the device. The light emitted in the range of 250-400 nm can be through one or more light emitting diodes (LEDs) that emit light in this range. For example, the device can include up to 20 LEDs emitting light in this range and they can be placed in the treatment portion of the device 185. These can be light emitters added in addition to the light emitters shown in, for example, FIG. 1E, or some of the light emitters in FIG. 1E could emit light in this disinfection range, or the light emitters can be configured to switch between treatment and disinfection emission ranges by control of the user, by automated setting of the device, at certain time ranges (e.g., disinfection for a period of time at the beginning or end of a treatment cycle), etc.

In one embodiment, the light emitter component 240 emits light using one or more light emitting diodes (LED). In other embodiments, the light emitter component 240 emits light using electric lamps, incandescent lamps, other electroluminescent lamps, or lasers. The light emitter component 240 is configured to emit light in the 600-1000 nm range, including the red portion and the near-infrared light portion of the spectrum, resulting in of the production of low-level laser light therapy. The light emitter component 240 can be designed to emit light in other ranges, as well, including less than or equal to 690 nm such as the visible spectrum. The emitted light is capable of applying thermal load on vaginal mucosa surrounding the device and light emitted in the visible spectrum provides an indication that the emitted light is applying thermal load in the non-visible spectrum.

In some embodiments, the light emitter component 240 includes one or more rings of optic segments such as light emitting diodes creating a helicopter optic configuration allowing radial distribution of light to the surrounding visual tissue in contact with the shell or a portion of the shell of the device. Thus, as one example, the light emitted from the device is emitted in a toroid shape or ring to illuminate a portion of the vaginal cavity rather than illuminating the entire vaginal cavity. In an alternative embodiment, the light emitted from the device is from a plurality of emitters coupled to the device. The plurality of emitters can be configured as lines or rows of emitters along the vertical axis 105 of, horizontal axis 110 of, or at a diagonal across the device or a portion of the device. In addition, the plurality of emitters can be configured as rings along the horizontal axis 110, the rings placed next to each other along the vertical axis 105. In some embodiments, the device includes manual or automatic click-by-click positionability in the vertical (axial) direction of this radial optic portion of the device, so that different axial stations within the vaginal mucosa may be treated at different points in time. In addition, it can include automated, repetitive vertical (axial) motion of this radial optic portion of the device, so that different axial stations within the vaginal mucosa may be treated in rapid sequence during the same treatment session.

In one embodiment, the light emitter component 240 includes one or more rings of a plurality of light emitting diodes that can move along the vertical axis 105 of the device. The position of the one or more rings of the plurality of light emitting diodes can be manually selected by the user. In the manual selection embodiment, the user can use a sliding button with a plurality of notches corresponding to positions along the vertical axis 105 of the device to select position of the one or more rings. In the automatic embodiment, the light emitter component 240 selects positions along the vertical axis 105 of the device based on one or more programmed patterns stored in memory 360. The one or more rings emitting light may be configured to apply thermal load on vaginal mucosa surrounding the device or a portion of the device.

In one embodiment, the emitted light is provided by an external light source or box piping in light through one or more assemblies or bundles of optical fiber cables. In another embodiment, the emitted light is provided by a central light emitter at one end of the device operating via free-space optical communication and directing light along the vertical axis 105, resulting in light exiting radially out of the transparent section peripheral to the inner wall of the shell of the device towards the vaginal tissue in contact with the shell of the device. For example, the inner wall of the shall may include a conical reflector including angled sides configured to reflect light such that the light is emitted radially out of the device towards the vaginal mucosa surrounding the device at an angle. The angle, for example, is normal to the outer shell of the device.

In one embodiment, the light emitter component 240 has a light configuration component 242. The light configuration component 242 is configured to increase the deposited energy density into the target tissue of vaginal muscles, which enhances the therapeutic effects of the light radiation provided by the device. The deposited energy density is a portion of the total energy generated by the LED emitters of the device. In one embodiment, the deposited energy density is represented by the energy density in mW/cm² units. In one embodiment, the light configuration component 242 is configured to concentrate the light emitted from the LED emitters by adding a focusing component, e.g., a lens assembly, on top of each LED emitter, which increases the optical power density being delivered from the LED emitters to the vaginal tissue contacted by the device without providing more electrical current to the LED emitters, without using disproportionately more battery power, without increasing the heat output from the LED emitters and without risking damage to the device or to the users of the device.

Figure 7:
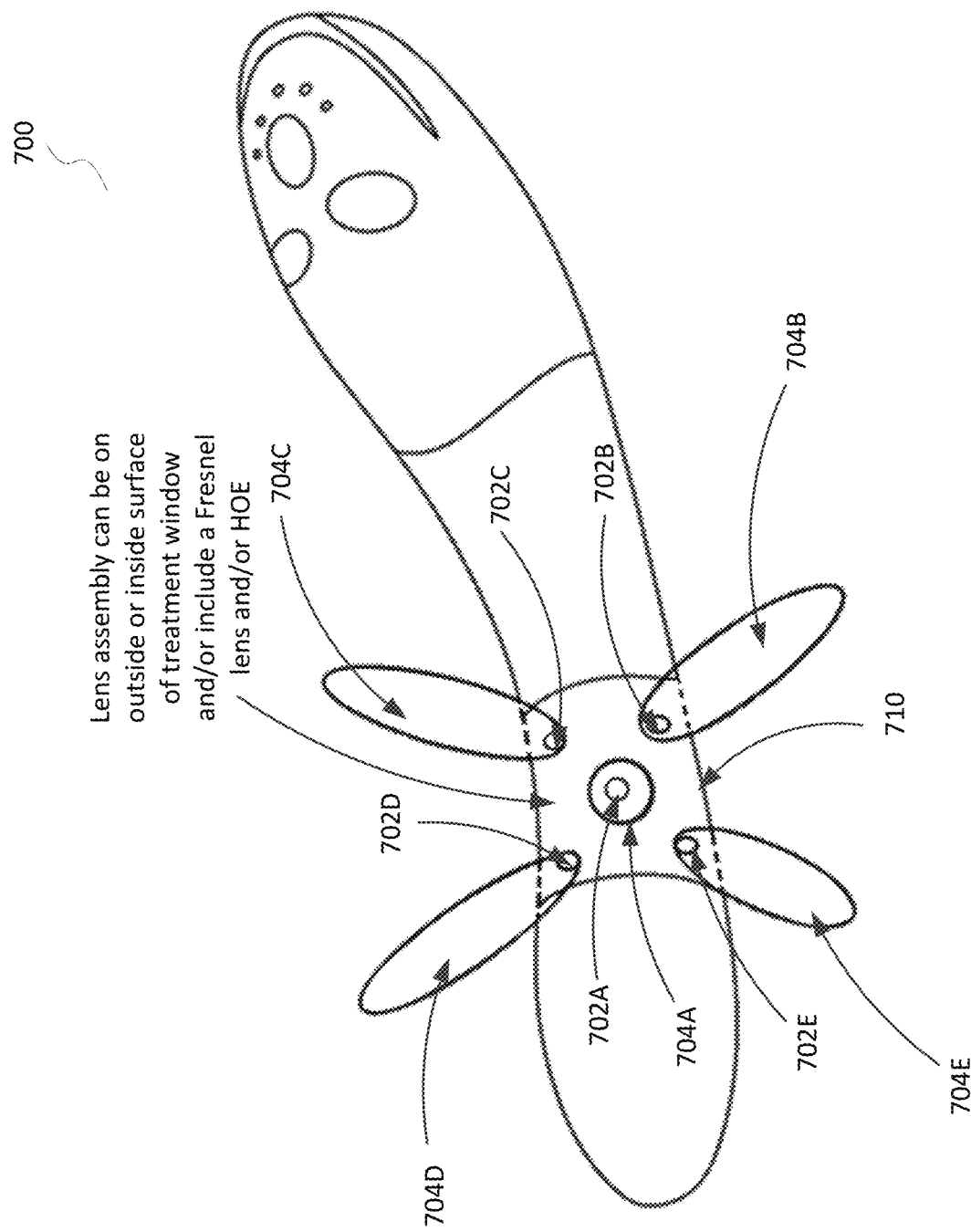
FIG. 7 shows an example of a rejuvenation and massage device providing increased energy density into target tissue of vaginal muscles through a light configuration component of the device, in accordance with an embodiment.

FIG. 7 shows an example of a rejuvenation and massage device 700, which provides increased energy density to target tissue of the vaginal muscles through the light configuration component 242 of the device. The device 700 shown in FIG. 7 has 5 LED emitters, 702A, 702B, 702C, 702D and 702E. Each of the LED emitters has a focusing component, e.g., a lens assembly, associated with (e.g., positioned above or over) the LED emitter. The focusing component can refract/bend light rays from the LED emitters. The light emitted from each of the light emitters is concentrated in a controlled area to form a focused beam of light, e.g., 704A, 704B, 704C, 704D and 704E, when it exits the transparent treatment window 710. The focused beam of light increases the optical power density being delivered to the vaginal tissue contacted by the device 700.

Figure 8B:
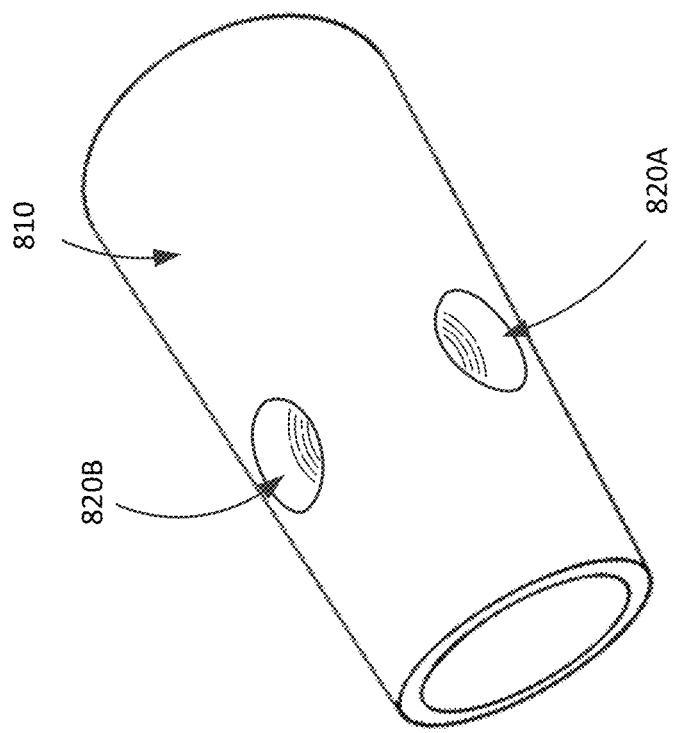
FIG. 8B shows an example of positioning a lens assembly in a concave configuration for each light emitter of the device on the outside surface of a transparent treatment window of the device, in accordance with an embodiment.
Figure 8A:
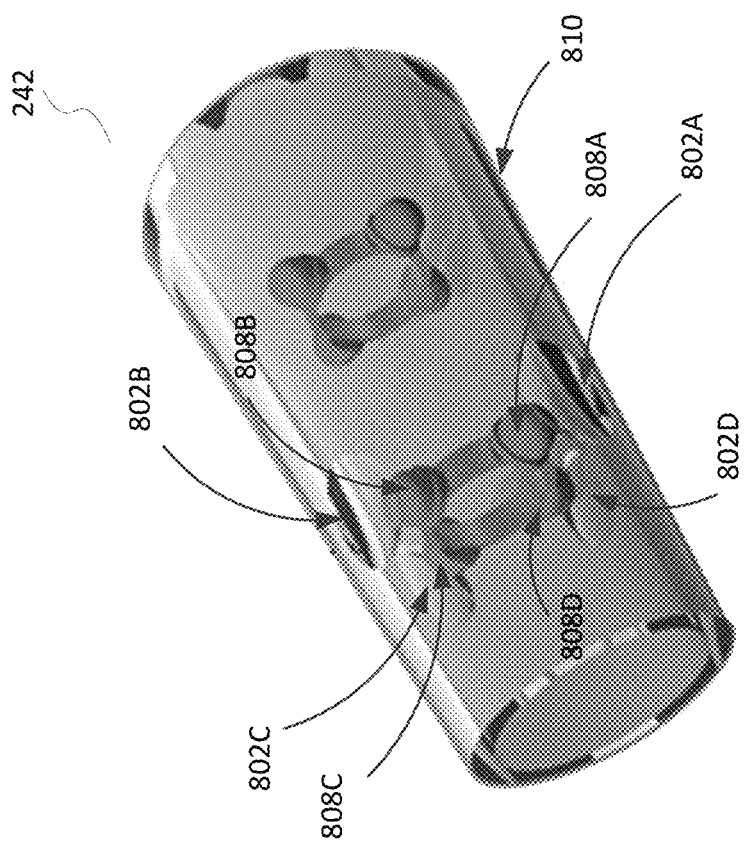
FIG. 8A shows a light emitting component having a light configuration component configured to use a lens assembly in a concave configuration for each light emitter of the device, in accordance with an embodiment.

The light configuration component 242 uses various types of a focusing components to increase the optical power density being delivered to the tissue, as illustrated in FIGS. 8A-8E. FIG. 8A shows an embodiment of the light emitting component 240 having a light configuration component 242 configured to position a lens assembly in a concave configuration for each LED emitter on top of a transparent treatment window 810. The light emitting component 240 shown in FIG. 8A includes multiple LED emitters, e.g., 808A-808D, arranged along a vertical axis inside the surface of the treatment window 810 such that the treatment window surrounds the light emitting component 240. Each of the LED emitters has one (or more) corresponding lens assembly in a concave configuration on top of each LED emitter, e.g., corresponding lens assembly 802A on top of the LED emitter 808A. The lens assembly 802A is a transparent concave lens, which can focus light emitted from the LED emitter 808A by refraction such that the beam of the focused light from the LED emitter 802A is targeted into vaginal tissues of the user of the device. The lens assembly on top of each LED emitter can be placed on the outside surface of the treatment window 810 or on the inside surface. FIG. 8B illustrates a perspective view of a lens assembly emitter in concave configuration (e.g., 820A) on the outside surface of the treatment window 810. In another embodiment, the concave lens can be placed on the inside surface of the treatment window 810.

Figure 8D:
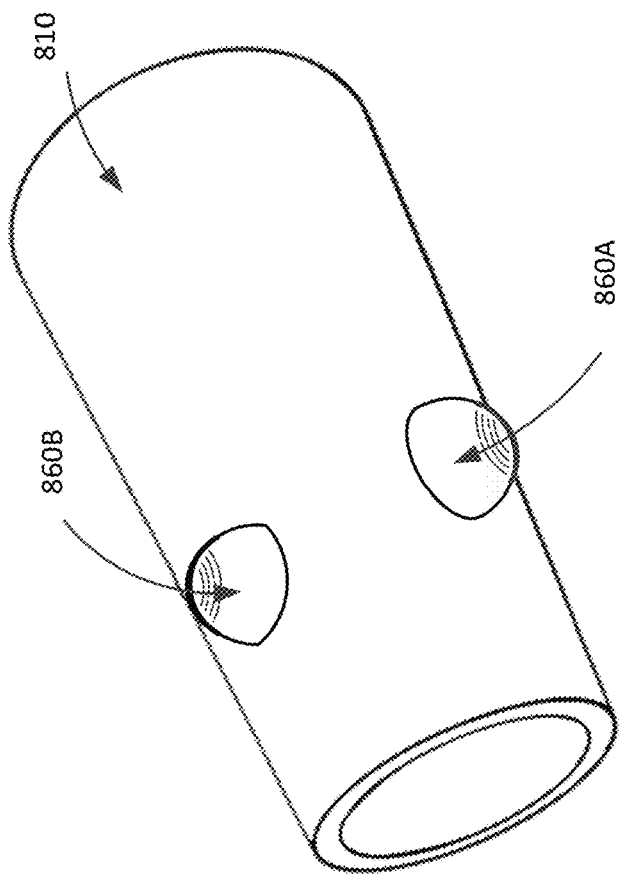
FIG. 8D shows an example of positioning a lens assembly in a convex configuration for each light emitter of the device on the outside surface of a transparent treatment window of the device, in accordance with an embodiment.
Figure 8C:
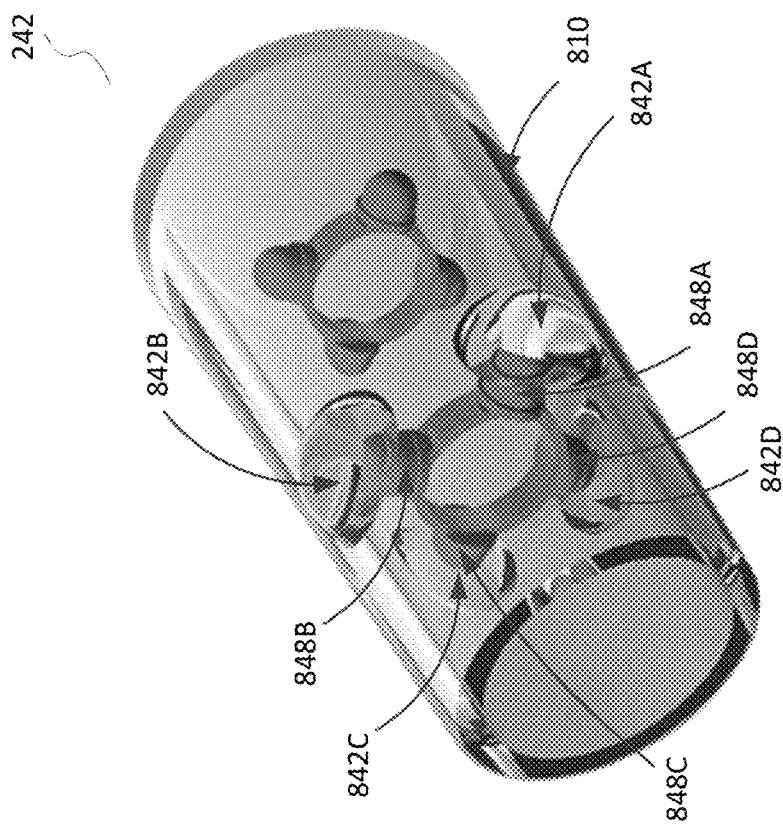
FIG. 8C shows a light emitting component having a light configuration component configured to use a lens assembly in a convex configuration for each light emitter of the device, in accordance with an embodiment.

In another embodiment, the light configuration component 242 includes a convex lens on top of each LED emitter. FIG. 8C shows an embodiment of the light emitting component 240 having a light configuration component 242 that is made up of a lens assembly in a convex configuration for each LED emitter of the device. The light emitting component 240 shown in FIG. 8C includes multiple LED emitters, e.g., 848A-848D, arranged along a vertical axis inside the surface of the treatment window 810. Each of the LED emitter has a corresponding lens assembly in a convex configuration on top of each LED emitter, e.g., corresponding lens assembly 842A on top of the LED emitter 848A. The lens assembly 842A is a transparent convex lens which can focus light emitted from the LED emitter 848A by refraction such that the beam of the focused light from the LED emitter 842A is targeted into vaginal tissues of the user of the device. The lens assembly 860A or 860B on top of each LED emitter can be placed on the outside surface of the treatment window 810 as shown in FIG. 8D. In another embodiment, the convex lens for a LED emitter can be positioned on the inside surface of the treatment window 810.

In some embodiments, the light configuration component 242 includes other focusing optical mechanisms as the focusing component instead of using the concave or convex lens described above. In one embodiment, a Fresnel lens with concentric/annular rings of tiny ridges is used as the focusing component of the light configuration component 242. The Fresnel lens acts to refract light in the same way as a standard lens, e.g., a concave or convex lens, but it allows for a much thinner format of the concave/convex lens. In one embodiment, a portion or an entire top and/or bottom surface of the transparent treatment window of the rejuvenating and massage device can be patterned via injection molding to effect appropriate focusing of the light emitted from the light emitters. In another embodiment, another optic mechanism after the injection molding can be added to effect appropriate focusing of the light emitted from the light emitters.

In yet another embodiment, a holographic optical element (HOE) is used as the focusing component in the light configuration component 242. HOE works via a process of constructive and destructive interferences to effect appropriate focusing of the light emitted from the light emitters of the rejuvenation and massage device. The HOE can be placed anywhere in the light path generated by the light emitted from the light emitters. For example, the HOE associated with the LED emitters of the device can be optimized to generate appropriate focusing of the light emitted from the light emitters in response to narrowband light waves (e.g., mono-color light waves like a laser). The HOE can be made very thin. For example, it can be as thin as a piece of paper. Similar to the Fresnel lens configuration described above, a portion or an entire top and/or bottom surface of the transparent treatment window of the rejuvenating and massage device can be patterned via injection molding to effect appropriate focusing of the light emitted from the light emitters. In another embodiment, other optic mechanisms can be added after the injection molding to appropriately focus the light emitted from the light emitters.

In some embodiments, the light configuration component 242 uses different types of plastics with different refractive indices positioned over the light emitters of the device to generate appropriate focusing of the light emitted from the light emitters. In other embodiments, the material of the focusing components of the light configuration component 242 can be non-plastic, for example, glass, liquids, vapor-deposited metal, semiconductor material, any other suitable material or the composite of thereof. In one embodiment, the light configuration component 242 is composed of material selected based on the wavelength of the lighted emitted from the LED emitters. A material selected from the materials mentioned above, which matches the wavelength of the light emitted from the LED emitters, can generate a high index of refraction of light such that the light emitted from the light emitters can be appropriately focused. Additionally, air or other gas like dry nitrogen can be introduced into the plastic material of the focusing component as a trapped bubble, or into the over molded silicone surface, to generate a focusing effect of the light emitted from the light emitters.

Figure 8E:
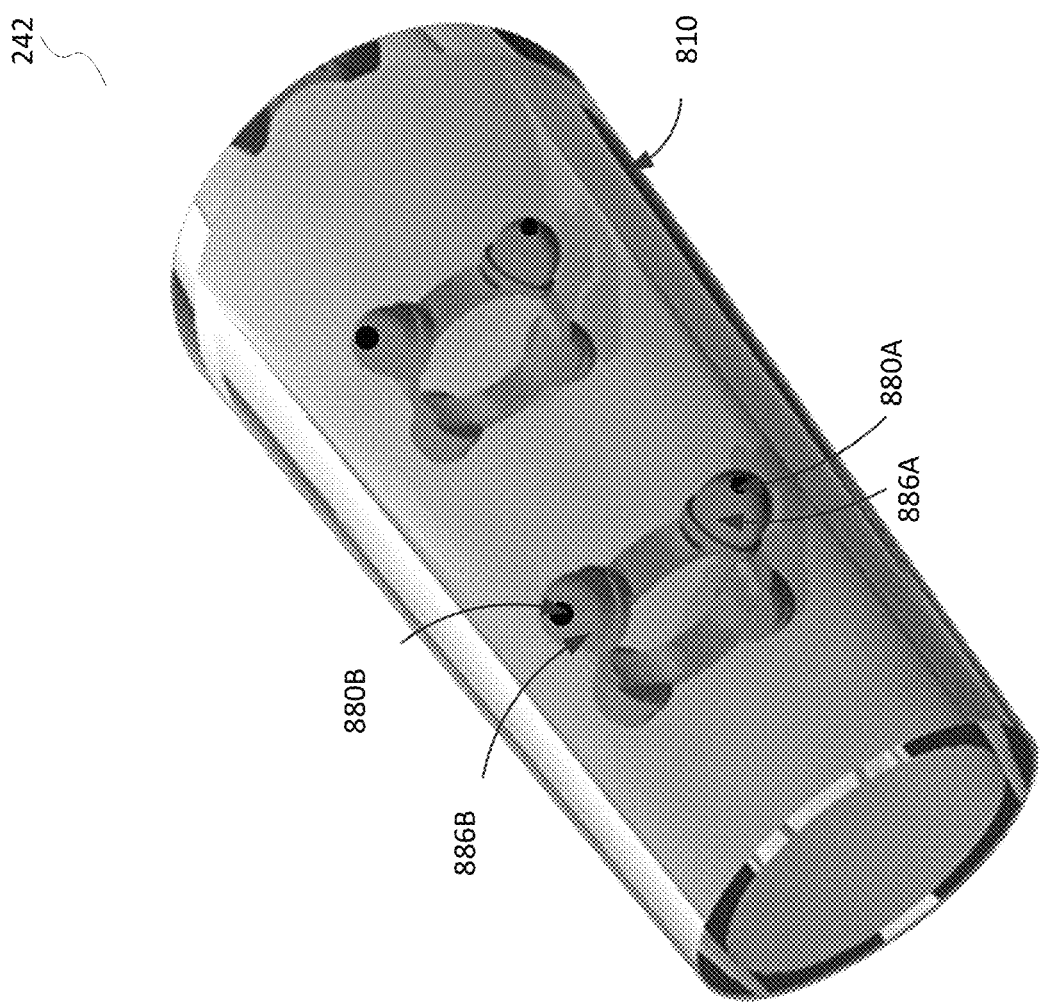
FIG. 8E shows an embodiment of a light configuration component in a pre-lensed configuration, in accordance with an embodiment.

The light configuration component 242 can also be the light emitters themselves according to one embodiment. For example, the LED emitters are micromachined or otherwise modeled prior to being integrated into the transparent treatment area of the device in such a way as to self-focus the light as the light passes through the transparent treatment area. FIG. 8E shows an embodiment of the light configuration component 242 in a pre-lensed configuration. In this embodiment, each of the LED emitters, e.g., 886A-886B, includes a corresponding pre-lensed component, e.g., 880A-880B. Each of the light emitters can be pre-lensed by micro-machinery or molding prior to integration into the transparent treatment area of the device. The pre-lensed light emitters can self-focus the light themselves to target the vaginal tissues when the light passes though the transparent treatment window 810.

It is noted that light being radiated into the human tissue tends to undergo intense scattering into a multiplicity of angles (e.g., described by the Henyey-Greenstein scattering coefficients), which implies extinction of photons of the light. The scattering of light broadens the volume of tissue being illuminated, therefore tending to further reduce the instantaneous optical power density delivered to a specific volume of tissue. The disclosed rejuvenation and massage device is advantageously configured to concentrate the light as it exits the power unit of the device and increase the power density being delivered to the tissue of vaginal muscles, which enhances the therapeutic effects of light radiation provided by the device. The pre-focused light generated by the light configuration module of the device before it enters the human tissue can offset at least a portion of the loss of power density on the human tissue caused by the intense scattering.

It is also noted that focusing the light from the light emitters of the rejuvenation and massage device increases the energy density of the light, but it may reduce the overall uniformity of illumination. However, the light emitters of the device can be selected to emit light into the tissue at a very wide angle. Therefore, the light configuration module 242 can be configured to adjust the emitting angle of each light such that the overall uniformity of illumination on the human tissue will not be appreciably reduced by focusing the light. Furthermore, the intense scattering of the light as described above tends to rehomogenize the light flux within the human tissue, therefore the slight non-uniformity caused by focusing the light is acceptable in terms of the enhancement of therapeutic effects of light radiation provided by the device.

Figure 9:
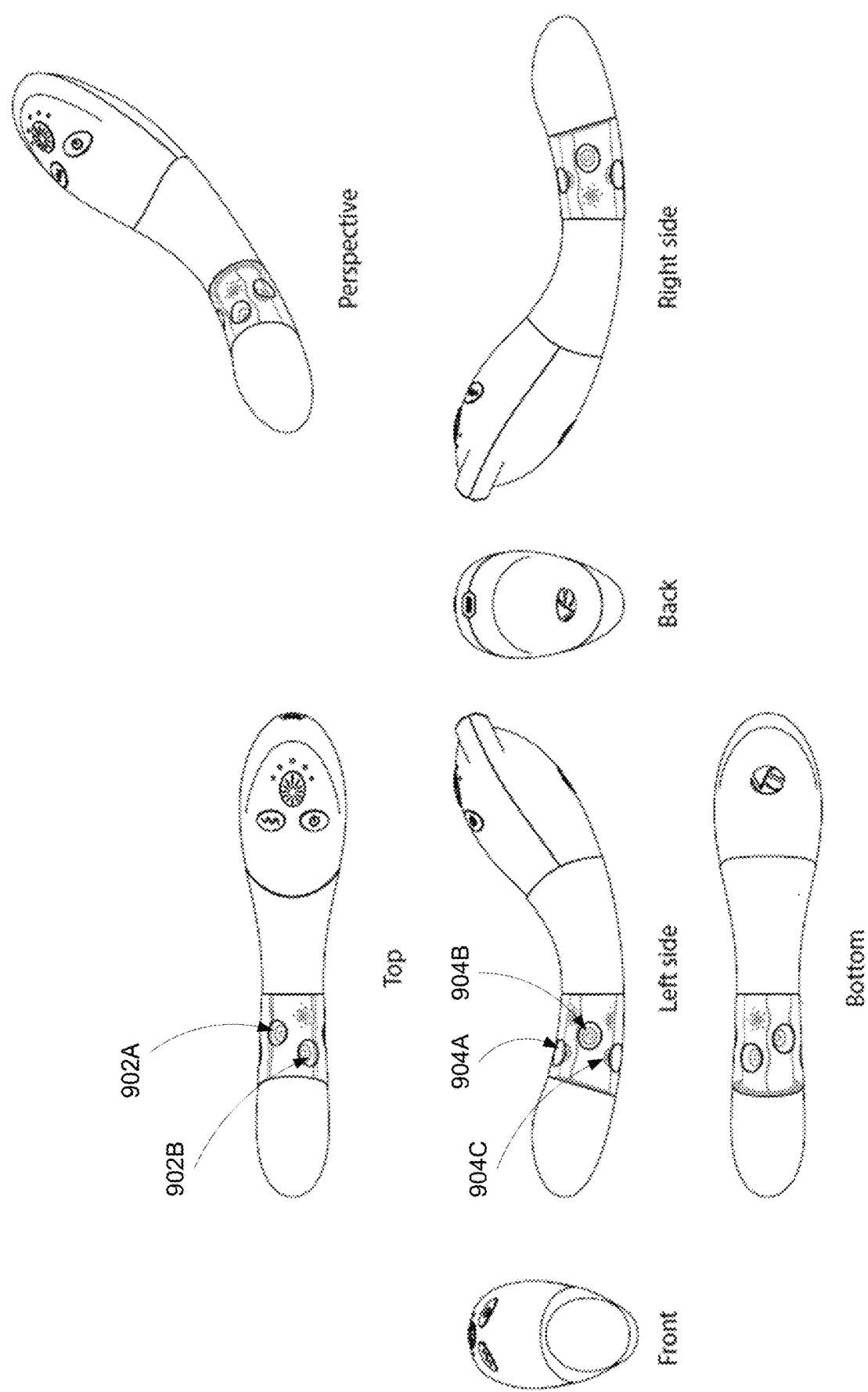
FIG. 9 shows examples of various views of a rejuvenation and massage device with enhanced light configuration, in accordance with an embodiment.

FIG. 9 shows examples of various views of a rejuvenation and massage device with enhanced light configuration, in accordance with an embodiment. The various views of the rejuvenation and massage device shown in include a top view, bottom view, front view, back view, left side view, right side view and a perspective view. The enhanced light configuration of the rejuvenation and massage device is provided by a light configuration component of the device. For example, in the top view, the device has two LED emitters each covered by a lens assembly, e.g., 902A and 902B. Similarly, in the left side view, the device had three LED emitters each covered by a lens assembly, e.g., 904A, 904B and 904C. The light configuration component of the device is configured to increase the deposited energy density into the target tissue of vaginal muscles by refracting the light coming out of the LED emitters. The increased deposited energy density delivered to the target tissue of the vaginal muscles enhances the therapeutic effects of the light radiation provided by the device.

Turning back to FIG. 2, the user interface 250 includes one or more buttons or controls for powering the device, selecting a vibration setting, turning on or off light therapy via LEDs, and turning on or off a light indicator setting in one embodiment. In another embodiment, the user interface 250 includes one or more buttons or controls for selecting a vibration setting, selecting a temperature setting, a duration setting, a temperature position setting, a light emitted position setting, or any combination thereof, though some embodiments may include only a subset of these settings or may include additional settings. The buttons may include sliding buttons with notches, pushbutton switches, switches, joysticks, keypads, tactile buttons, toggle switches, rocker switches, slide switches, trackballs, microswitches, or other types of controls. In one embodiment, the buttons or controls are at least greater than half a centimeter in diameter and of a color contrasting a color of the material of the device for visibility. The user interface 250 can also include a visual indicator via one or more LEDs indicating status of treatment such as whether treatment is currently happening, treatment duration, temperature associated with treatment, or any other suitable indicator of treatment via light therapy, vibration, or any combination thereof. For example, the visual indicator can turn on if treatment is occurring and turn off if treatment is not occurring. The visual indicator can also be a bar and how much of the bar is lit up using LEDs can indicate duration of treatment (e.g., in minutes) or temperature of treatment (e.g., indicates whether temperature is too low, just right, or too high).

The power source 260, in one embodiment, includes a low voltage power line from the device to a plug-in wall transformer. In other embodiments, the power source 260 includes a radio frequency or other charging apparatus built into the device and one or more batteries. Thus, the power source 260 can couple to a charging apparatus or charger through a universal serial bus (USB) connection such as a Micro-B plug, UC-E6 proprietary (non-USB) plug, Mini-B plug, Standard-A receptacle, Standard-A plug, Standard-B plug, micro USB or any other suitable connector including one or more pins necessary to charge the device. The charging apparatus can be configured to couple to a wall wart alternating current (AC) plug. Charger 150 in FIG. 1D is one example of such a charger. Other charging systems can also be used. For example, the device might use replaceable batteries, might be wirelessly or inductively charged via a base that includes a transmitting coil that magnetically couples with a receiving coil in the device to induce current in the receiving coil and charge the device.

In addition to the device examples provided above, a variety of other designs can be used. Some embodiments include a rejuvenation and massage device capable of stimulating neocollagenesis and neoelastogenesis factors, while simultaneously engaging the female sexual response in order to maximize likelihood of repeated use of the product and thence assure clinical benefit. Some embodiments include a rejuvenation and massage device based on the combination of light energy to effect collagen melting, denaturation and remodeling. Further embodiments include a rejuvenation and massage device based on the combination of light energy to effect collagen melting, denaturation and remodeling, with simultaneous vibration designed to enhance subsequent myofibril generation and neocollagenesis.

Additional embodiments include a rejuvenation and massage device based on the combination of light energy to produce an LLLT effect. The device can also be a rejuvenation and massage device based on the combination of light energy to produce an LLLT effect, with simultaneous vibration designed to enhance subsequent myofibril generation and neocollagenesis. Similarly, any of these device designs can be enhanced by being used in association with a customized medical-grade lubricant, designed to match the refractive index of the optical emitting surface to the tissue surfaces in order to maximize light transmission into the tissue and minimize optical scattering loss.

Any of these designs can also be over-the-counter, Class 1 devices to effect light-assisted vaginal rejuvenation, (as opposed to bulky, expensive, professional clinical units). Furthermore, any of these designs can include a high-efficiency resonant drive mechanism based on periodically-unbalanced permanent-magnetic fields, designed to minimize electrical loss while maximizing transmission of mechanical vibration to selected portions of the device structure. Thus, the device disclosed in FIGS. 1 and 2 can be modified to include components specific to any of these different device designs.

Figure 3:
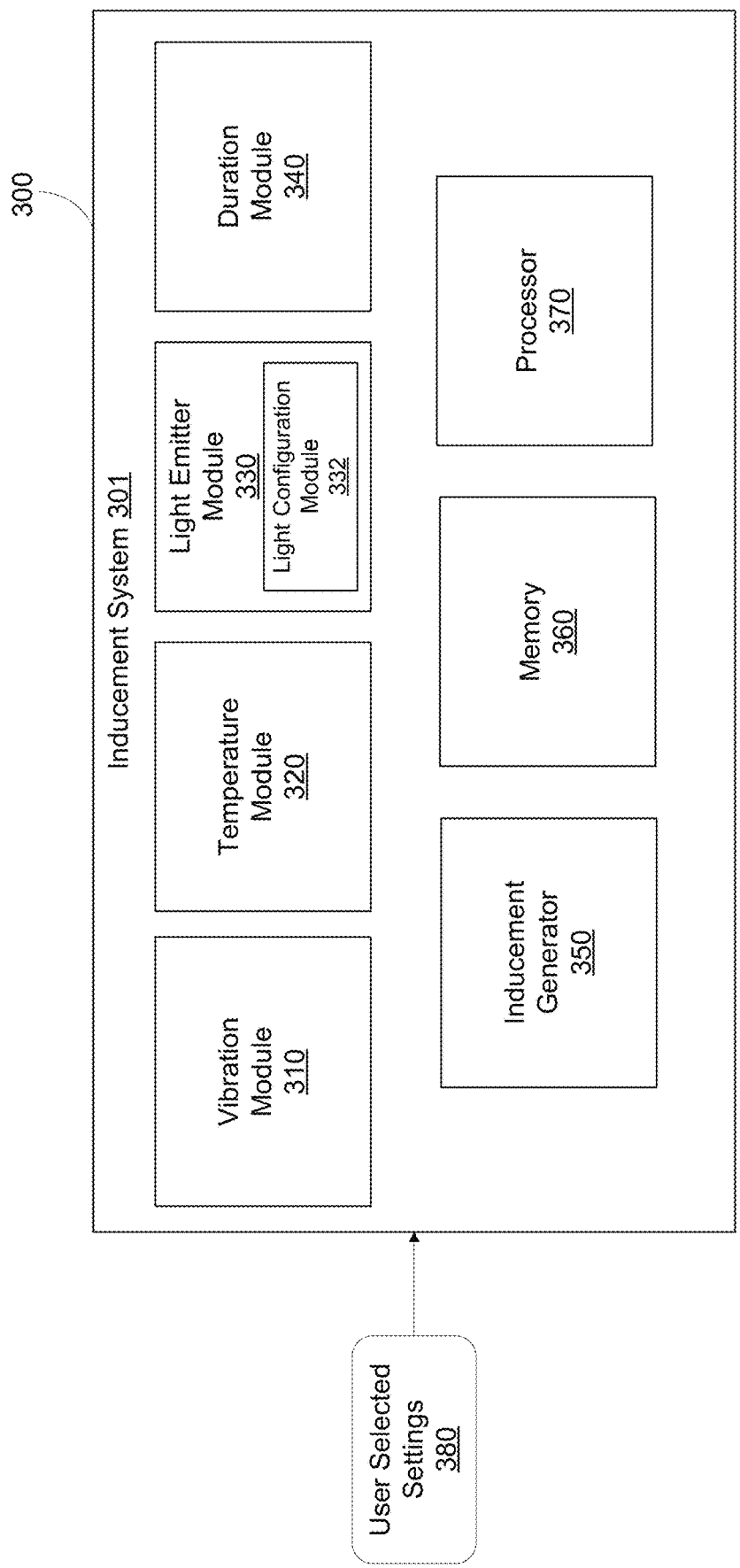
FIG. 3 is a block diagram of an inducement environment for inducing neocollagenesis, neoelastogenesis, and neofibrogenesis by the rejuvenation and massage device illustrated in FIG. 2, in accordance with an embodiment.

(c) Neocollagenesis, Neoelastogenesis, Neofibrogenesis, and Pleasure Inducing System and Method FIG. 3 is an example of an embodiment of an inducement environment 300 for inducing neocollagenesis, neoelastogenesis, and neofibrogenesis by the rejuvenation and massage device illustrated in FIG. 2. The inducement environment 300 includes an inducement system 301 and user selected settings 380 as an input to the inducement system 301. The inducement system 301 includes software modules including a vibration module 310, a temperature module 320, a light emitter module 330 having a light configuration module 332, a duration module 340, an inducement generator 350, memory 360 and a processor 370. The inducement system 301 receives the user selected settings 380 and, based on the user selected settings 380, determines range of vibration, duration of use, range of thermal load, and amount of emitted light to ensure inducement of neocollagenesis, neoelastogenesis, and neofibrogenesis. In alternative embodiments, the inducement system 301 includes additional and/or alternative components than the components shown in FIG. 3.

The user selected settings 380 include a vibration setting, a temperature setting, a duration setting, a temperature position setting, a light emitted position setting, or any combination thereof. In one embodiment, the user selected settings 380 are sent to the inducement generator 350 to be sent to the other modules in the inducement system 301. In another embodiment, the user selected settings 380 are sent directly to the corresponding modules. For example, the vibration setting is sent to the vibration module 310, the temperature setting to the temperature module 320, the duration setting to the duration module 340, the temperature position setting to the temperature module 320, and the light emitted position setting to the light emitter module 330.

Example vibration settings include a low setting, medium setting, and a high setting for a plurality of patterns including no vibration, constant vibration, pulse vibration, and wave vibration. The low, medium and high setting increase strength of vibration for the plurality of patterns. Example temperature settings include various percentages of LEDs being turned on (e.g., 0%, 25%, 50%, 75%, 100%, etc.). Example duration settings include how many minutes to turn the vibration and/or temperature on such as 1 minute, 5 minutes, 10 minutes, etc. Temperature position settings and light emitted position settings can be optionally provided and include options to indicate which portion of LEDs to turn on or off and, in the embodiment where the safety temperature component 220 provides heat as well, which portion of the device to provide additional heat from the safety temperature component 220.

In the embodiment where the user selected settings 380 are sent to the inducement generator 350, the inducement generator 350 determines settings for the corresponding modules that it sends as instructions to the corresponding modules. For example, if the user has only selected one setting, the inducement generator 350 determines settings for the other modules based on the one selected setting. For example, if the user has selected a vibration setting, depending on the frequency of the setting or a protocol for treatment, the duration can be decreased if the vibration frequency is higher than a threshold frequency or can be increased if the vibration frequency is lower than the threshold frequency. If the user has selected a temperature setting, the duration can be increased or decreased based on whether or not the selected temperature is lower than or higher than a threshold temperature, respectively. If the user has selected a duration setting, depending on the interval of time selected by the duration setting, the temperature setting can be set above or below a threshold temperature based on whether or not the interval of time selected is below or above a threshold interval of time. In one embodiment, the duration setting is not an option available to the user and has a default run time, such as 5 minutes. The vibration setting can also be set dependent on the conditions of the duration setting.

The vibration module 310 receives instructions for a vibration setting from the inducement generator 350, according to one embodiment. The vibration module 310 applies a selected vibration setting, if the user selected a vibration setting, or a default vibration setting in a range of 5-10 Hz if no vibration setting is selected by the user. In one embodiment, the default vibration setting includes vibration in the range of 5-10 Hz and vibration in the range of 1-15 kHz.

The temperature module 320 receives instruction for a temperature setting from the inducement generator 350, according to one embodiment. If the user has selected a temperature setting, the temperature module 320 turns on or off one or more LEDs of the light emitter component 240. In another embodiment where the safety temperature component 220 and the cooling component 230 are included in the device, the temperature module 320 also adjusts thermal load and cooling to maintain the thermal load in the selected temperature setting. The temperature module 320 maintains the thermal load applied by the light emitter component 240, the thermal load component 220, the cooling component 230, or any combination thereof such that temperature induced by the thermal load is in a range of 35° C.-80° C. or 35° C.-41° C. as a default. The temperature module 320 may maintain the thermal load such that the temperature induced is in the desired range through a local dosimetry device. If the received instruction includes a temperature position setting, the temperature module 320 sends instructions regarding position to the light emitter component 240, the safety temperature component 220, or any combination thereof in various embodiments. The temperature module 320 will detect thermal overload and automatically shut down the device if thermal overload is detected.

The light emitter component 240 of the device provides a radiative thermal load from the light emission to penetrate and stimulate the tissue to a depth of 5 mm and, thus, the device also provides a conductive thermal load to tissue directly in contact with the device. The heat generated by the light emitter component 240 will heat the device and thus the shell of the device. Then, the shell of the device is maintained at an acceptable temperature that can be monitored by the device (e.g., by the safety temperature component 220). The temperature of the shell of the device can also be high enough to warm cells in the vaginal mucosa at a depth of 3 to 5 mm with the transfer of energy from the radiative warming via the light emitter component 240. In one embodiment, the safety temperature component 220 can also include a temperature sensor that monitors temperature of vaginal mucosa at a depth of up to 7 mm. The temperature sensor can monitor temperature in the range of 60° C.-80° C., which enhances collagen rejuvenation.

The light emitter module 330 emits light in designed wavelengths including red and/or near-infrared portions of the spectrum lying between 600-1,000 nm as well as in the visible light spectrum. In another embodiment, light is emitted at wavelengths covering a spectral range of 635-980 nm as well as in the visible light spectrum. In yet another embodiment, light is emitted at wavelengths covering a spectral range of 670-810 nm as well as in the visible light spectrum, and in another embodiment, light is emitted at singular wavelengths alone, such as 670 nm or 808 nm as well as in the visible light spectrum. In the embodiment where moveable ring-optics are used to emit light radially, the light emitter module 330 determines the position of the ring-optics along the vertical axis 110 of the device. In one embodiment, the position may be determined automatically to ensure continuous exposure of the vaginal tissue in contact with the device to the emitted light. In another embodiment, the user selects the light emitted position setting. Then, the light emitter module 330 repositions the ring-optics according to the light emitted position setting. The device can also be programmed via instructions in memory 360 to emit light in the visible spectrum responsive to light in the non-visible spectrum being emitted. Therefore, the user has a visual indicator indicating emission of light in the non-visible spectrum.

In one embodiment, the light emitter module 330 has a light configuration module 332 to increase the deposited energy density into the target tissue of vaginal muscles of a user of the device. The light configuration module 332 stores executable computer program instructions, and when executed by the processor 370, the light configuration module 332 is configured to focus the light as the light is emitted from the light emitters of the device and passes though the treatment window of the device. In one embodiment, the light configuration module 332 is associated with a light configuration component, such as a focusing component, which can be located on the outside or inside surface of the treatment window and over a corresponding light emitter.

The duration module 340 counts clock cycles while the device is in use. If the user has selected a duration setting, the duration module 340 will shut down the device after the corresponding number of clock cycles has been reached or gives an indication once the duration setting has been reached. Alternatively, based on protocol for treatment and therapy as stored in the memory 360 of the device, the duration module 340 shuts down a function of the device (e.g., vibration, light emission, etc.) if a threshold duration as dictated by the protocol is reached.

The inducement system 301 includes a memory 360 and a processor 370. The memory 360 includes a non-transitory computer-readable storage medium that stores computer-executable instructions for carrying out the functions attributed to the inducement system 301. The memory 360 may additionally store settings and default settings for the vibration component, safety temperature component, light emitter component, and duration component. The default settings can be dictated by a protocol for treatment and therapy.

The processor 370 processes data signals and may include various computing architectures including a complex instruction set computer (CISC) architecture, a reduced instruction set computer (RISC) architecture, or an architecture implementing a combination of instruction sets. Although only one processor is shown in FIG. 3, multiple processors may be included. The processors can include an arithmetic logic unit, a microprocessor, a general purpose computer, or some other information appliance equipped to transmit, receive and process electronic data signals from the memory 360 and other devices both shown and not shown in the figures. In operation, the processor 370 loads and executes the instructions stored in the memory 360 to carry out the inducement process described herein. An embodiment of a process performed by the inducement system 301 is described further below in conjunction with FIG. 4.

Figure 4:
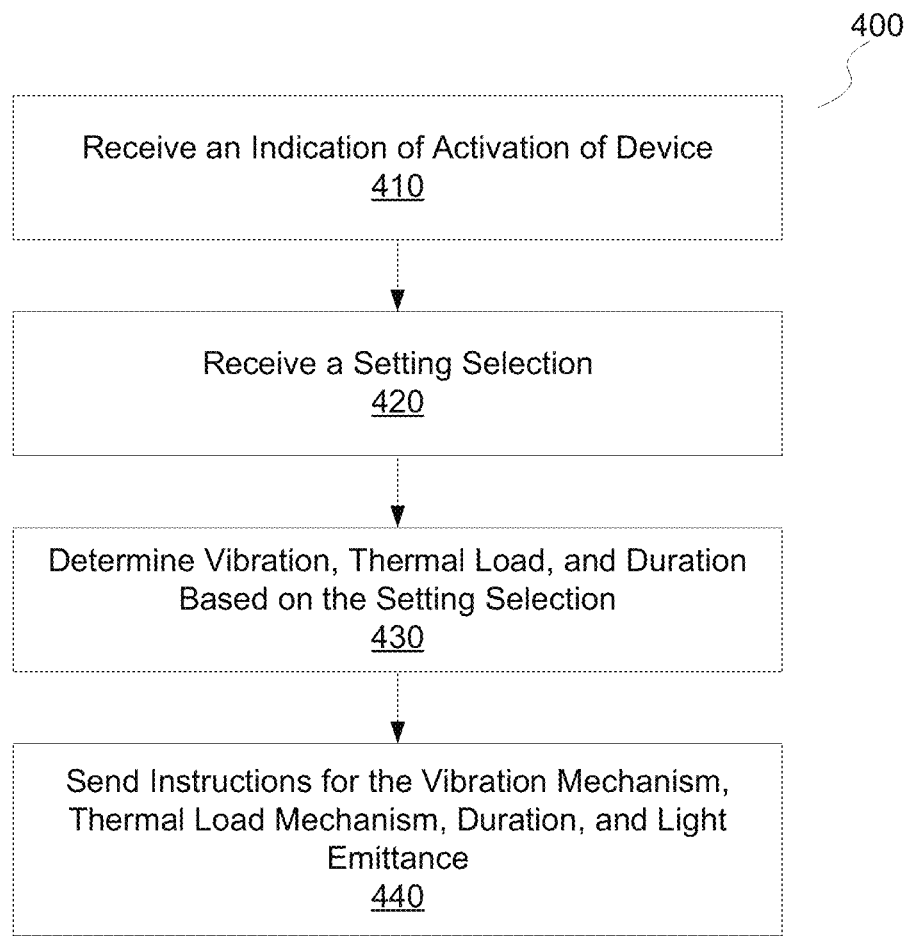
FIG. 4 is a flowchart of a method for inducing neocollagenesis, neoelastogenesis, and neofibrogenesis, in accordance with an embodiment.

FIG. 4 is a flowchart of one embodiment of a method 400 for vaginal rejuvenation. In other embodiments, the method may include different and/or additional steps than those shown in FIG. 4. The functionality described in conjunction with the inducement environment 300 in FIG. 3 may be provided by the inducement generator 350 in the inducement system 301 or may be provided by any other suitable component, or components, in other embodiments.

In one embodiment, the method 400 is a sequential process starting with remodeling of the ECM including collagen and elastin and ending with effecting fibrotic responses to assist in remodeling of the ECM, consequently tightening the vaginal tissue and vaginal lumen. In another embodiment, the method 400 remodels the ECM while simultaneously effecting fibrotic responses to assist in remodeling the ECM and consequently tightening the vaginal tissue and vaginal lumen.

An indication is received 410 by the inducement system 301 that a user has activated the rejuvenation and massage device. The indication may include notification that the device has been placed into contact with vaginal tissue from a sensor used to detect contact between the device and vaginal tissue. Contact of vaginal tissue with the device or presence of vaginal tissue within a threshold distance with the device can also be detected using optical sensors, capacitive sensors (detecting capacitive proximity), as well as any other suitable proximity sensor. The indication could also be a notification that the user has turned on the device or activated a particular setting.

Setting selections are received 420 (e.g., from the user or from a controller in the device itself if the device is automatically providing settings) to control a mechanism of the device. For example, the user may select a vibration speed or pattern. In one embodiment, no setting selections are selected by the user and, in another embodiment, one or more setting selections are selected. In a further embodiment, the setting selection by the user is a default selection for the device. The device itself can also determine the setting, so the setting might be received 420 from a component or controller in the device. Based on the setting selections, vibration, thermal load, and duration are determined 430. If the user has selected a vibration setting, the device will vibrate at the selected vibration setting. If the user has selected a thermal load setting, the device will thermally load the surrounding vaginal tissue at the thermal load setting via the light emitter component 240, the safety temperature component 220, the cooling component 230, or any combination thereof. If the user has selected a duration setting, the device will operate for the selected duration setting. Similarly, if the instructions regarding the setting were received 420 within the device in an automatic setting selection mode, the device will institute the setting. In other embodiments, if no setting selections or not all setting selections are selected by the user, a default setting for each setting with no user setting selection will be determined. Instructions including the determined settings for vibration, thermal load, and duration as well as light emittance are sent 440.

Figure 5:
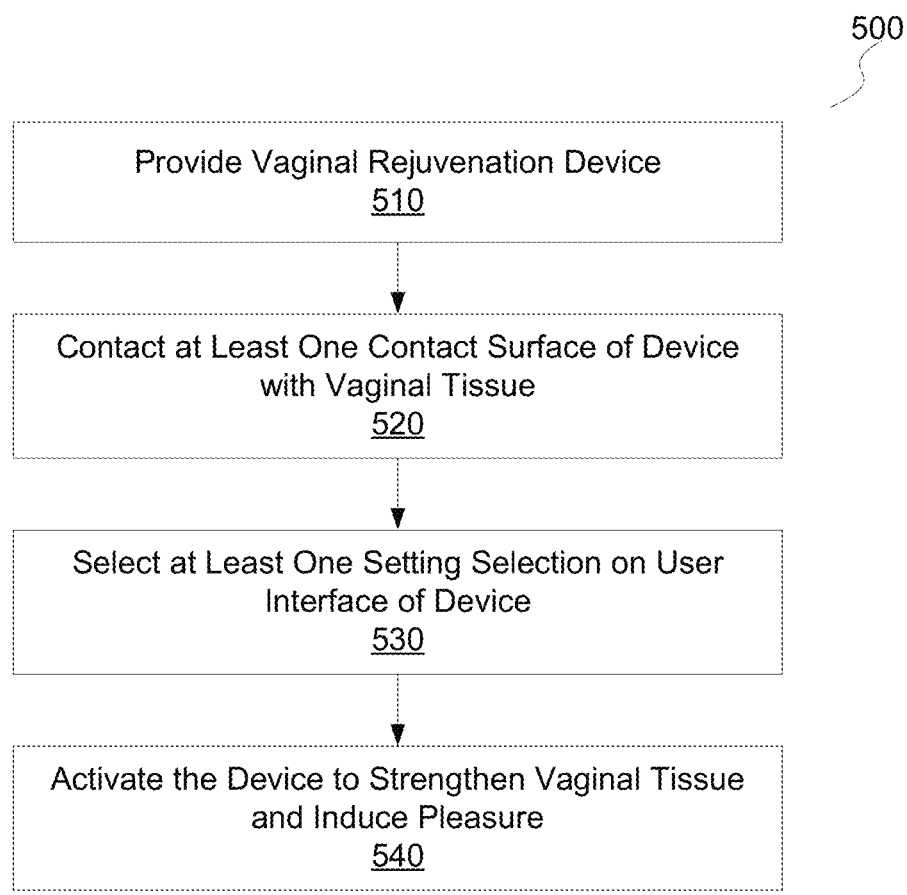
FIG. 5 is a flowchart of a method for vaginal rejuvenation performed by a user of an embodiment of the device, such as in FIGS. 1C-1E, in accordance with an embodiment.

FIG. 5 is a flowchart of one embodiment of a method 500 for vaginal rejuvenation performed by a user of the device. A device, such as or an embodiment of the device described in FIGS. 1C-1E with one or more components as described in FIG. 2, is provided 510. The user provides 510 the insertable vaginal rejuvenation device (e.g., one of the devices described above or other devices) and contacts 520 at least one contact surface of the insertable device with mucosa tissue such as vaginal tissue. Next, the user selects 530 at least one setting selection on the user interface of the device. In one embodiment, the selections available to the user include a vibration setting, a temperature setting, a duration setting, a temperature position setting, a light emitted position setting, and any combination thereof, as described with regard to FIG. 3. To strengthen vaginal tissue and simultaneously induce pleasure, the user activates 540 the device. Alternatively, the user activates 540 one or more settings indicating turning on vibration, light emission, or any combination thereof.

Figure 6:
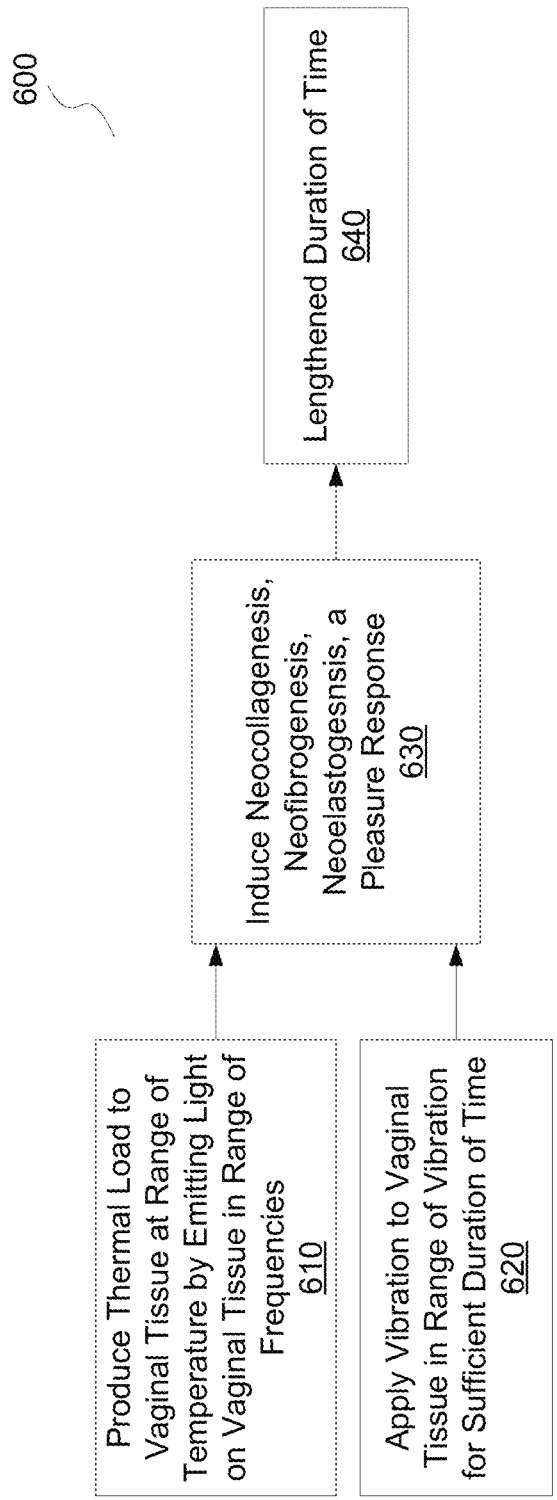
FIG. 6 is a flowchart of a method for an overall physiological process resulting from use of an embodiment of the device, such as in FIGS. 1C-1E, in accordance with an embodiment.

FIG. 6 is a flowchart of one embodiment of a method 600 for the overall physiological process resulting from use of a device of any of the embodiments described in FIGS. 1C-1E. Thermal load is produced 610 to the vaginal tissue through light emission on the vaginal tissue and vibration is applied 620 to the vaginal tissue. All of these steps may be performed or only one or two of these steps may be performed. The thermal load is produced 610 at a sufficient rate to effect a temperature within the deep vaginal mucosa ranging from 35° C.-80° C., and more particularly between 35° C.-41° C. and/or 60° C.-80° C., as described in FIG. 3. The light is emitted in a range of 600-1000 nm as well as in the visible light spectrum, as described in FIG. 3. Also as described in FIG. 3, vibration is applied 620 at a range of 1-15 kHz and can also be applied 620 at a range of 5-10 Hz. Producing 610 thermal load by emitting light and applying 620 vibration at a range of 5-10 Hz for a sufficient duration of time induces 630 neocollagenesis, neofibrogenesis, or neoelastogenesis. In addition, applying 620 vibration at a range of 1-15 kHz induces 630 a pleasure response in the vaginal tissue. The induced pleasure response results in a lengthening 640 of the duration of time during which the thermal load is produced 610 to the vaginal tissue relative to the duration of time that thermal load could be produced 610 without the induced 630 pleasure response.

(d) Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Any of the steps, operations, or processes described herein may be performed or implemented with one or more hardware or software modules, alone or in combination with other devices. In one embodiment, a software module is implemented with a computer program product including a computer-readable medium containing computer program code, which can be executed by a computer processor for performing any or all of the steps, operations, or processes described.

The apparatus described herein may be specially constructed for the required purposes, and/or it may include a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

The documents cited below and throughout are hereby incorporated by reference herein in their entireties for all purposes.

REFERENCES

1. DeLancey J O, Morgan D M, Fenner D E, Kearney R, Guire K, Miller J M, Hussain H, Umek W, Hsu Y, Ashton-Miller J A. Comparison of levator ani muscle defects and function in women with and without pelvic organ prolapse. Obstetrics & Gynecology 109:295-302, 2007.
2. Lukacz E S, Lawrence J M, Contreras R, et al. Parity, mode of delivery, and pelvic floor disorders. Obstetrics & Gynecology 2006; 107:1253.
3. Varma M G, Brown J S, Creasman J M, et al. Fecal incontinence in females older than aged 40 years: who is at risk? Diseases of the Colon & Rectum 2006; 49:841.
4. Boreham M K, Richter H E, Kenton K S, et al. Anal incontinence in women presenting for gynecologic care: prevalence, risk factors, and impact upon quality of life. American Journal of Obstetrics & Gynecology 2005; 192:1637.
5. Fultz N H, Burgio K, Diokno A C, et al. Burden of stress urinary incontinence for community-dwelling women. American Journal of Obstetrics & Gynecology 2003; 189:1275.
6. Olsen A L, Smith V J, Bergstrom J O, et al. Epidemiology of surgically managed pelvic organ prolapse and urinary incontinence. Obstetrics & Gynecology 1997; 89:501.
7. D. D. Rahn, J. F. Acevedo, and R. A. Word, Effect of vaginal distention on elastic fiber synthesis and matrix degradation in the vaginal wall: potential role in the pathogenesis of pelvic organ prolapse, AJP—Regu Physiol October 2008 Vol. 295 No. 4R1351-R1358.
8. Leikina, E., et al., 2002. Proc. Natl. Acad. Sci. USA. doi 10.1073/pnas.032307099.
9. Kei Hayashi, George Thabit III, Kathleen L. Massa, John J. Bogdanske, A. J. Cooley, John F. Orwin and Mark D. Markel, The Effect of Thermal Heating on the Length and Histologic Properties of the Glenohumeral Joint Capsule, American Journal of Sports Med 1997 25: 107.

10. Chang R. Physical Chemistry for the Chemical and Biological Sciences. 3rd Ed. Sausalito, Calif.: University Science Books; 2000:470.
11. Kushikata N, Negishi K, Tezuka Y, et al. Is topical anesthesia useful in noninvasive skin tightening using radiofrequency? Dermatologic Surgery 2005; 31: 526-33.
12. Kei Hayashi, DVM, MS, Janet A. Nieckarz, BS, George Thabit III, MD, John J. Bogdanske, BA, A. J. Cooley, DVM, and Mark D. Markel, DVM, PhD, Effect of Nonablative Laser Energy on the Joint Capsule: An In Vivo Rabbit Study Using a Holmium:YAG Laser, Lasers in Surgery and Medicine 20:164-171 (1997).
13. Tirkkonen L, et al., The effects of vibration loading on adipose stem cell number, viability and differentiation towards bone-forming cells, Journal of the Royal Society Interface 2011; 8(65): 1736-1747.
14. Prè, D, et al., High-Frequency Vibration Treatment of Human Bone Marrow Stromal Cells Increases Differentiation toward Bone Tissue, Hindawi Publishing Corporation, Bone Marrow Research, Volume 2013, Article ID 803450, 13 pages.
15. C. H. Lee, H. J. Shin, I. H. Cho et al., Nanofiber alignment and direction of mechanical strain affect the ECM production of human ACL fibroblast, Biomaterials, Vol. 26, No. 11, pp. 1261-1270, 2005.
16. M. Chiquet, M. Matthisson, M. Koch, M. Tannheimer, and R. Chiquet-Ehrismann, Regulation of extracellular matrix synthesis by mechanical stress, Biochemistry and Cell Biology, Vol. 74, No. 6, pp. 737-744, 1996.
17. E. Ruoslahti, Stretching is good for a cell, Science, Vol. 276, No. 5317, pp. 1345-1346, 1997.
18. Fagnani, F, et al., The effects of a whole-body vibration program on muscle performance and flexibility in female athletes. American Journal of Physical Medicine & Rehabilitation 85: 956-962, 2006.
19. Takeuchi, R, et al., Effects of vibration and hyaluronic acid on activation of three-dimensional cultured chondrocytes, Arthritis Rheum. 2006 June; 54(6):1897-905.
20. Wang, C Z, et al., Low-magnitude vertical vibration enhances myotube formation in C2C12 myoblasts, Journal of Applied Physiology Sep. 1, 2010 Vol. 109 No. 3 840-848.
21. Rodrigues dos Santos, R, et al., The low-level laser therapy on muscle injury recovery: literature review, J Health Sci Inst. 2010; 28(3):286-8.

What is claimed is:

1. A device for tissue rejuvenation therapy, the device comprising:
   a handle portion composed at least partially of an opaque material and an insertable portion;
   a light emitting subsystem, the light emitting subsystem comprising:
      a set of light emitters radially distributed about a longitudinal axis within the insertable portion, and
      a set of focusing components, positioned at the insertable portion, that are configured to focus light emitted from the set of light emitters onto a mucosa tissue during operation to provide adjustment of light transmission to the mucosa tissue; and
   a vibration mechanism comprising a vibration motor that is configured to transmit vibration to the mucosa tissue.

2. The device of claim 1, further comprising a safety temperature component comprising a thermocouple assembly configured to be in thermal communication with the mucosa tissue, through the insertable portion, during operation.

3. The device of claim 2, wherein the safety temperature component is configured to detect that a thermal condition of the mucosa tissue satisfies a threshold condition, wherein the device is configured to adjust light emitted by the set of light emitters in response to the thermal condition.

4. The device of claim 1, wherein the vibration mechanism comprises a resonant drive motor flexibly coupled to a distal portion of the handle portion.

5. The device of claim 1, wherein the set of light emitters are further configured to provide a treatment mode in which the set of light emitters emit light in a first wavelength range, and a sterilization mode in which the set of light emitters emit light in a second wavelength range, wherein the device is operable to transition between the treatment mode and the sterilization mode.

6. The device of claim 1, wherein the set of light emitters comprises a set of rings of light emitting diodes distributed along the longitudinal axis.

7. The device of claim 6, wherein a subset of the set of rings is configured to be transitioned into an activated state upon receiving an input at a control device in communication with the light emitting subsystem.

8. The device of claim 1, further comprising a component enclosed within the insertable portion and extending along a length of the insertable portion, the set of light emitters arranged around the component.

9. The device of claim 8, wherein each focusing component of the set of focusing components includes a portion at each light emitter positioned between the light emitter and a wall of the insertable portion and being configured to focus light from the light emitter.

10. The device of claim 9, wherein each focusing component of the set of focusing components also includes a portion on a treatment window formed on a wall of the insertable portion, the portion comprising a lens.

11. The device of claim 1, further comprising a cooling subsystem comprising at least one of a reservoir of cryogenic fluid and a Peltier cooler thermally coupled to the insertable portion.

12. The device of claim 1, wherein a transparent portion of the insertable portion forms a band around a circumference of the insertable portion through which light is emitted from the set of light emitters.

13. The device of claim 1, further comprising a proximity sensor coupled to the insertable portion, wherein the proximity sensor is configured to detect contact between tissue and the device during operation.

14. A device for tissue rejuvenation therapy, the device comprising:
   a handle portion composed at least partially of an opaque material and an insertable portion;
   a light emitting subsystem within the insertable portion, the light emitting subsystem comprising:
      a set of light emitters radially distributed about a longitudinal axis within the insertable portion, the set of light emitters comprising at least one light emitter configured for providing treatment to a tissue and at least one light emitter configured as a visual indicator of operation of the device, and
      a set of focusing components, positioned at the insertable portion, that is configured to focus light emitted from the set of light emitters onto the tissue during operation;
   a safety temperature component comprising a thermocouple assembly in thermal communication with the insertable portion; and a vibration mechanism comprising a vibration motor within the insertable portion of the insertable body.

15. The device of claim 14, wherein the safety temperature component further comprises a heating element configured to be in thermal communication with a mucosa tissue, through the insertable portion, during operation.

16. The device of claim 14, wherein the insertable portion is configured for a lubricant matching a refractive index of a wall of the insertable portion.

17. The device of claim 14, wherein the vibration mechanism comprises a resonant drive motor flexibly coupled to a distal end of the handle portion.

18. The device of claim 14, wherein the set of light emitters comprises a set of rings of light emitting diodes distributed along the longitudinal axis.

19. The device of claim 18, further comprising a component enclosed within the insertable portion and extending along a length of the insertable portion, the component having a smaller diameter than the insertable portion, the set of rings of light emitting diodes arranged around the component.

20. The device of claim 14, further comprising a cooling subsystem comprising at least one of a reservoir of cryogenic fluid, a heat pipe, and a Peltier cooler thermally coupled to the insertable portion, wherein the set of light emitters are configured to transmit light onto the tissue, during operation, to provide thermal adjustment to the tissue to a first penetration depth in association with tissue restoration; and wherein at least one of the cooling subsystem and the safety temperature component is configured to provide thermal adjustment to the tissue, during operation, to a second penetration depth in association with perceived discomfort reduction.

21. The device of claim 14, wherein a transparent treatment band is formed around a circumference of a wall of the insertable portion, the transparent treatment band flanked on a side by the opaque material of the handle portion.

22. The device of claim 14, further comprising a proximity sensor coupled to the insertable portion, wherein the proximity sensor comprises at least one of an optical sensor and a capacitive sensor, and is configured to detect contact between the tissue and the device during operation.

23. The device of claim 14, wherein the set of focusing components further comprises a set of lenses at the insertable portion.

* * * * *

UNITED STATES PATENT AND TRADEMARK OFFICE
CERTIFICATE OF CORRECTION

PATENT NO. : 11,116,691 B2  
APPLICATION NO. : 16/201941  
DATED : September 14, 2021  
INVENTOR(S) : Courtion et al.

It is certified that error appears in the above-identified patent and that said Letters Patent is hereby corrected as shown below:

On the Title Page

Item (56), in Column 2, under "Other Publications", Line 1, delete "U.S" and insert -- U.S. --, therefor.

Item (57), in Column 2, under "Abstract", Line 12, delete "though" and insert -- through --, therefor.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*